US008005708B2

(12) United States Patent
Cho et al.

(10) Patent No.: US 8,005,708 B2
(45) Date of Patent: Aug. 23, 2011

(54) DATA VERIFICATION PROGRESS MANAGING AND SUPPORTING SERVER

(75) Inventors: Jinshu Cho, Saitama (JP); Kazumoto Ochi, Kawaguchi (JP); Kotonari Aoki, Kita (JP); Akishi Murase, Funabashi (JP); Toshihiro Tamaru, Koto (JP); Nobuhiko Okada, Koto (JP)

(73) Assignee: Fujitsu FIP Corporation, Tokyo (JP)

( * ) Notice: Subject to any disclaimer, the term of this patent is extended or adjusted under 35 U.S.C. 154(b) by 1425 days.

(21) Appl. No.: 10/432,363

(22) PCT Filed: Nov. 30, 2001

(86) PCT No.: PCT/JP01/10518
§ 371 (c)(1),
(2), (4) Date: Nov. 5, 2003

(87) PCT Pub. No.: WO02/44973
PCT Pub. Date: Jun. 6, 2002

(65) Prior Publication Data
US 2004/0068692 A1    Apr. 8, 2004

(30) Foreign Application Priority Data
Dec. 1, 2000    (JP) .................................. 2000-367714

(51) Int. Cl.
*G06Q 10/00*    (2006.01)
(52) U.S. Cl. ...................................... 705/7.32; 705/7.29
(58) Field of Classification Search .................. 705/7.32
See application file for complete search history.

(56) References Cited

U.S. PATENT DOCUMENTS

| 5,666,490 | A | * | 9/1997 | Gillings et al. | ............... 709/238 |
| 5,764,923 | A | * | 6/1998 | Tallman et al. | ................... 705/3 |
| 5,893,909 | A | | 4/1999 | Nomura et al. | |
| 6,082,776 | A | * | 7/2000 | Feinberg | ........................ 283/72 |

(Continued)

FOREIGN PATENT DOCUMENTS

EP    0 669 600 A2    8/1995
(Continued)

OTHER PUBLICATIONS

Hunt et al, "Effects of Computer-Based Clinical Decision Support Systems on Physician Performance and Patient Outcomes", JAMA, Oct. 21, 1998, vol. 280, No. 15.*

(Continued)

*Primary Examiner* — Romain Jeanty
*Assistant Examiner* — Thomas Mansfield
(74) *Attorney, Agent, or Firm* — Kratz, Quintos & Hanson, LLP

(57) ABSTRACT

The object of the present invention can be achieved by the data verification supporting server for supporting verification of data which is inputted to each item of a survey form for surveying an effect of implementing a product, including a survey form managing part managing the survey form sent from an implementer terminal of an implementer, with a revised number of the survey form; a re-survey information managing part informing the implementer of a re-survey inquiry based on a re-survey inquiry request for requesting a re-survey, which is received from a verifier terminal of a verifier verifying the survey form, the re-survey inquiry request indicating the implementer who sent the survey form; and a survey form maintaining part maintaining the survey form and the version information managed by the survey form managing part when notification of a verification completion of the survey form is received from the verifier terminal.

3 Claims, 31 Drawing Sheets

U.S. PATENT DOCUMENTS

| | | | |
|---|---|---|---|
| 6,151,581 A * | 11/2000 | Kraftson et al. | 705/3 |
| 6,526,388 B1 | 2/2003 | Sakaguchi et al. | 705/8 |
| 6,574,621 B1 * | 6/2003 | Lautzenheiser et al. | 707/4 |
| 6,820,235 B1 * | 11/2004 | Bleicher et al. | 715/236 |
| 6,834,285 B1 * | 12/2004 | Boris et al. | 707/103 R |
| 6,839,678 B1 | 1/2005 | Schmidt et al. | 705/3 |
| 2002/0049727 A1 * | 4/2002 | Rothkopf | 707/1 |
| 2002/0198748 A1 * | 12/2002 | Eden et al. | 705/7 |

FOREIGN PATENT DOCUMENTS

| | | |
|---|---|---|
| EP | 0 936 566 A2 | 8/1999 |
| JP | 06-083844 | 3/1994 |
| JP | 6-83844 | 3/1994 |
| JP | 7-239945 | 9/1995 |
| JP | 07-311764 | 11/1995 |
| JP | 7-311764 | 11/1995 |
| JP | 9-97286 | 4/1997 |
| JP | 09-097286 | 4/1997 |
| JP | 10-214294 | 8/1998 |
| JP | 10-308810 | 11/1998 |
| JP | 10-320490 | 12/1998 |
| JP | 11-154185 | 6/1999 |
| JP | 11-261550 | 9/1999 |
| JP | 2000-148882 | 5/2000 |
| JP | 2001-118016 | 4/2001 |
| JP | 2001-142989 | 5/2001 |
| JP | 2001-188876 | 7/2001 |
| JP | 2001-312557 | 11/2001 |
| WO | WO 99/63473 | 12/1999 |

OTHER PUBLICATIONS

Nadkarni et al, "Managing Attribute-Value Clinical Trials Data Using the ACT/DB Client-Server Database System", JAMIA, 1998, 5, 139-151.*

The Canadian Office Action for corresponding Canadian patent application No. 2,430,971, dated Nov. 16, 2006.

Computer System for Clinical Trial; Electronic Publishing Company Japan; vol. 11, No. 8, Aug. 20, 2000, which including partial English translation, 11 pages.

Japanese Office Action dated Feb. 17, 2009.

Kawabe, Kanemi: "PMS Network System" Clinics & Drug Therapy vol. 13, No. 11, pp. 76-79, Dec. 1, 1994. (with partial English translation).

"Fujitsu S Family GCP/PMS Support System Components (Case Management) Manual" Fujitsu Co., Ltd., p. 1-15, Jul. 31, 2005. (with partial English translation).

Japanese Office Action dated Aug. 25, 2009.

Haruo Hayami, et al., "Inter-workflow Management and Support" NTT R&D Dec. 10, 1996, vol. 45, No. 12, p. 1301-1314. (With partial English translation).

Japanese Office Action issued on Feb. 2, 2010.

Japanese Office Action issued on Feb. 16, 2010.

Australian Patent Office communication for corresponding Australian Patent Application No. 2002218519 dated Dec. 23, 2004, with an International Preliminary Examination Report (Previously submitted May 30, 2003).

Murakami et al.: "An information system for supporting the clinical development and post-marketing investigation activities of novel drugs" Hitachi Hyoron, vol. 78, No. 4, pp. 65-70, Apr. 1, 1996.

Kyoichi Kimura: "Outline of novel drug investigation management system" IRYO-To-Computer, vol. 11, No. 9, pp. 40-45 Sep. 20, 2000.

Japanese Patent Office Action dated Mar. 28, 2006.

Chester King et al. "Medus/A: Distributing Database Management for Medical Research"; Computer Networks. Washington, Sep. 20-23, 1982, Digest of Papers from Compcon. Fall, Computer Society International Conference, New York, I.E.E.E., US, vol. Conf. 25, Sep. 20, 1982, pp. 635-642, XP002065364.

Supplementary European Search Report dated Jul. 3, 2007.

The Japanese Patent Office Action for corresponding Japanese patent application No. 2002-547066, dated Nov. 7, 2006.

* cited by examiner

FIG.3

| OPERATING PROCEDURE NO. | OPERATION OBJECT MAIN OPERATION | STATUS OF MEDICAL DOCTOR | STATUS OF PHARMACEU-TICAL MANUFACTURER |
|---|---|---|---|
| 24 | MEDICAL DOCTOR → INPUT PATIENT INFORAMTION | NOT SEND | — |
| 25 | MEDICAL DOCTOR → SURVEY FORM | SENT | NEW ARRIVAL |
| 26 | PHARMACEUTICAL MANUFACTURER CONFIRM SURVEY FORM INFORMATION → | MANUFACTURER RECEIVED | CONFIRMING |
| 27 | PHARMACEUTICAL MANUFACTURER REQUEST RE- SURVEY → | NEW ARRIVAL | REQUESTING |
| 28 | MEDICAL DOCTOR MODIFY SURVEY FORM INFORMATION → | NOT SEND | REQUESTING |
| 29 | MEDICAL DOCTOR SEND SURVEY FORM INFORMATION → | SENT | NEW ARRIVAL |
| 30 | PHARMACEUTICAL MANUFACTURER CONFIRM SURVEY FORM INFORMATION → | MANUFACTURER RECEIVED | CONFIRMING |
| 31 | PHARMACEUTICAL NAMUFACTURER COMPLETE SURVEY FORM → | MANUFACTURER RECEIVED | COMPLETED |
| 90 | PHARMACEUTICAL MANUFACTURER SET COLLECTION NOT-AVAILABLE → | MANUFACTURER RECEIVED | NOT AVAILABLE |

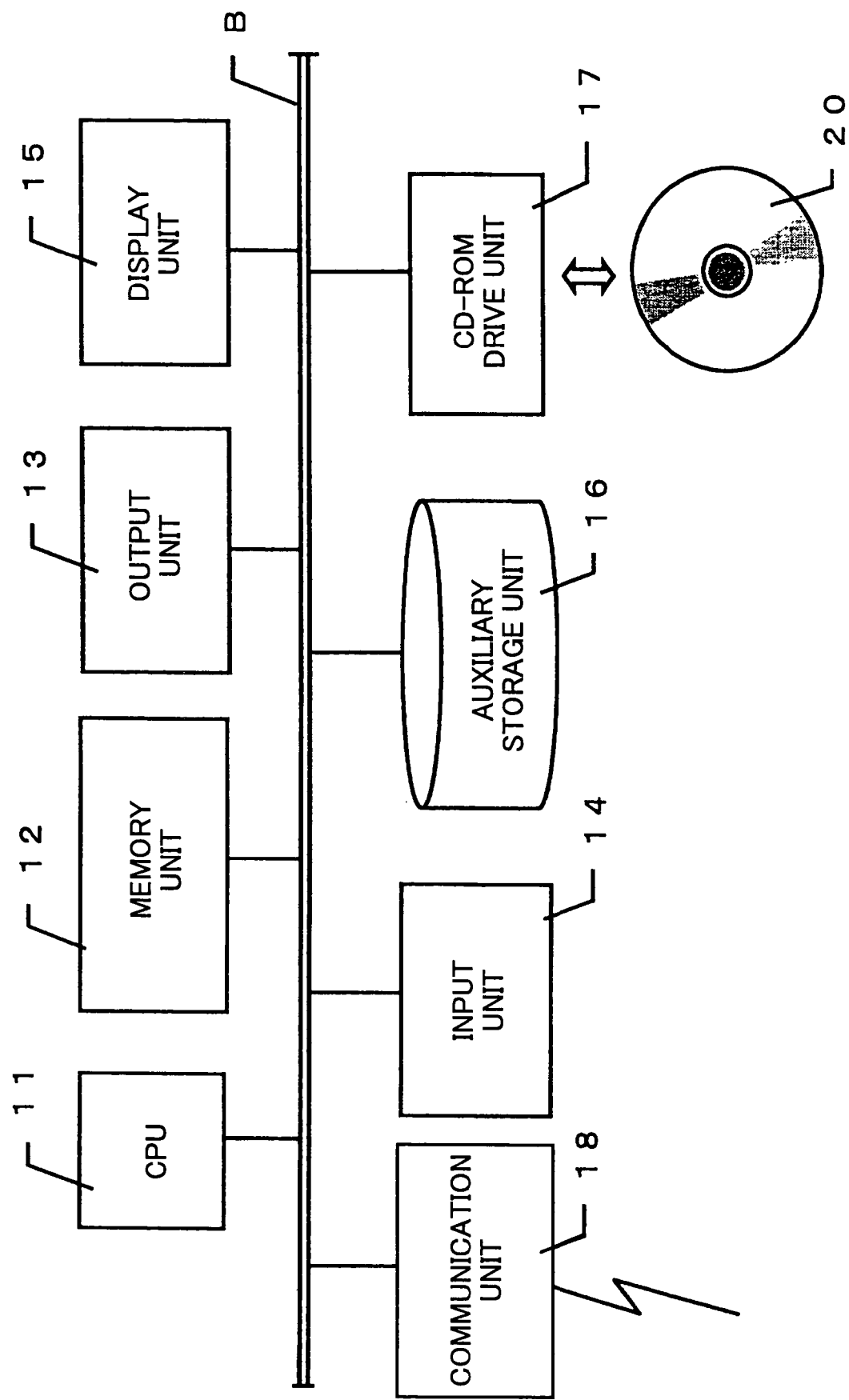

FIG.8

| 500 SURVEY FORM MANAGEMENT | | | | | | | | | | | □ ⊡ ☒ |
|---|---|---|---|---|---|---|---|---|---|---|
| SEARCH CONDITION | | | | | | | | | | 5001 |

| 510 | PROTOCOL | 502 ▼ | | BRANCH NAME | | | | | | |
|---|---|---|---|---|---|---|---|---|---|---|
| | ☐ NON REQUESTED INSTITUTION | | | MR NAME | | | | | | |
| 504 | REQUESTED DATE | | | INSTITUTION NAME | 505 | | | | | |
| | CONTRACT EXPIRATION DATE | | | DOCTOR NAME | | 506 SEARCH 507 | | | | |

510 — NEW CONTRACTUAL INSTITUTION INPUT
511 — CONTRACTUAL INSTITUTION INFORMATION UPDATE
512 — INPUT REQUEST/REMINDER
513 — MEDICAL DOCTOR IN CHARGE CHANGE

5002

| | | | | | | | | | | 516 SURVEY FORM STATUS | | | |
|---|---|---|---|---|---|---|---|---|---|---|---|---|---|
| 514 | REQUESTED DATE REMINDED DATE | INSTITUTION NAME SURVEY REQUESTED INSTITUTION No. | BRANCH NAME MR IN CHARGE | CONTRACTED DATE | CONTRACT TERM | CONTRACT CASE | MEDICAL DOCTOR NAME (SECTION NAME) | OBTAINED | NEW ARRIVAL | CONFIRMING | REQUESTING | COMPLETION/ NOT AVAILABLE |
| 515 | ☐ 2000/01/01 2000/01/02 | ABC HOSPITAL 00001 | EAST JAPAN BRANCH FUJIMI, ICHIRO | 2000/01/01 | 2000/10/10 2001/10/10 | 150 | IYAMA, SHIRO(PHYSICIAN) ×○ ○○(PHYSICIAN) △○ ○○(PHYSICIAN) | 1 8 1 | 1 5 0 | 1 0 0 | 1 0 0 | 1 0 0 |
| | ☐ | □□□□HOSPITAL 00002 | □□□□BRANCH □□ □□ | 2000/01/01 | 2000/10/10 2005/10/10 | 15 | □□ □□(PHYSICIAN) ×□ □□(PHYSICIAN) △□ □□(PHYSICIAN) | 1 0 0 | 1 1 0 | 0 1 1 | 0 1 1 | 0 1 1 |
| | ☐ 2000/01/01 2000/01/02 | △△△△HOSPITAL 00003 | △△△△BRANCH △△ △△ | 2000/01/01 | 2000/10/10 2005/10/10 | 10 | △△ △△(PHYSICIAN) ○△ △△(PHYSICIAN) | 1 0 | 0 1 | 1 1 | 1 1 | 1 1 |
| | ☐ | ××××HOSPITAL 00004 | ××××BRANCH ×× ×× | 2000/01/01 | 2000/10/10 2005/10/10 | 15 | ×× ×××(PHYSICIAN) □× ×××(PHYSICIAN) | 1 2 | 0 1 | 1 1 | 1 1 | 1 1 |

520 — CONTRACTUAL INSTITUTION INPUT

SAVING PROCESS IS NORMALLY COMPLETED. ~525
PROTOCOL : MEDICINE ABC USAGE RESULT SURVEY ~524

- 521 — [SAVE] SAVE INSTITUTION/MEDICAL DOCTOR INFORMATION ⎫
- 522 — [DELETE] DELETE INSTITUTION/MEDICAL DOCTOR INFORMATION ⎬ 5201
- 523 — [BACK] GO BACK TO PREVIOUS SCREEN ⎭

| SURVEY REQUEST INSTITUTION NO. | | | CONTRACTED DATE | 20000101 |
|---|---|---|---|---|
| CONTRACT TERM | 2000110 ~ 20011010 | | CONTRACT CASE(S) | 150 |
| INSTITUTION NAME | ABC HOSPITAL | | INSTITUTION CODE | |
| BRANCH NAME | EAST JAPAN BRANCH | | BRANCH CODE | |
| MR INCHARGE | FUJIMI, ICHIRO | EMPLOYEE CODE | 001 | E-Mail tro.@sei.fjp |

5202

MEDICAL DOCTOR INFORMATION

| DELETE | USER ID | NAME | SECTION NAME | SECTION CODE |
|---|---|---|---|---|
| ☐ | DOC1 | IYAMA, SHIRO | PHYSICIAN | 002 |
| NEW | | | | |
| NEW | | | | |
| NEW | | | | |
| NEW | | | | |

PROTOCOL SELECTION

| PROTOCOL NAME | INSTITUTION NAME SECTION NAME | CONTRACT TERM | CONTRACT CASE | INPUT CASE | NEW ARRIVAL | NOT SENT | SENT | NEW REGISTRATION |
|---|---|---|---|---|---|---|---|---|
| MEDICINE ABC PHARMACEUTICAL MANUFACTURER 1 | ABC HOSPITAL | 2000/10/10 2001/10/10 | 150 | 0 | 0 | 0 | 0 | NEW |
| MEDICINE ABC PHARMACEUTICAL MANUFACTURER 1 | TOKYO HOSPITAL PSYCHIATRIC SECTION | 2000/01/01 2000/01/01 | 10 | 0 | 0 | 0 | 0 | NEW |
| MEDICINE ABC PHARMACEUTICAL MANUFACTURER 1 | YAMANOTE HOSPITAL PHYSICIAN | 2000/02/01 2000/02/03 | 200 | 1 | 0 | 1 | 0 | NEW |
| MEDICINE ABC PHARMACEUTICAL MANUFACTURER 1 | ○○ GENERAL HOSPITAL | 2000/02/29 2001/02/29 | 12 | 1 | 1 | 0 | 0 | NEW |
| MEDICINE LMN PHARMACEUTICAL MANUFACTURER 6 | ABC HOSPITAL | 2000/10/18 2001/10/19 | 60 | 4 | 1 | 3 | 0 | NEW |
| MEDICINE LMN PHARMACEUTICAL MANUFACTURER 6 | YAMANOTE HOSPITAL PHYISICIAN | 2000/07/15 2001/05/30 | 140 | 0 | 0 | 0 | 0 | NEW |
| MEDICINE LMN PHARMACEUTICAL MANUFACTURER 6 | ○○GENERAL HOSPITAL | 2000/10/01 2000/10/02 | 0 | 14 | 1 | 6 | 7 | NEW |
| MEDICINE XYZ PHARMACEUTICAL MANUFACTURER 8 | TOKYOHOSPITAL PSYCHIATRIC SECTION | 2000/01/01 2000/01/01 | 14 | 0 | 0 | 0 | 0 | NEW |
| MEDICINE XYZ PHARMACEUTICAL MANUFACTURER 8 | ○○GENERAL HOSPITAL | 2000/01/01 2000/01/01 | 100 | 0 | 0 | 0 | 0 | NEW |

FIG.12A

PATIENT INFORMATION INPUT — 610

PROTOCOL NAME: MEDICINE ABC
INSTITUTION NAME: ABC HOSPITAL
PLEASE INPUT PATIENT INFORMATION

| PATIENT NAME (KATAKANA) | FAMILY NAME | FUJI | GIVEN NAME | TARO |
|---|---|---|---|---|
| INITIALS(NAME) | TF | INITIAL CONVERSION | | |
| GENDER | MALE ▽ | | | |
| BIRTH DATE | A.D. ▽ | 2000 YY | 1 MM | 1 DD |
| CHART NO. | (INPATIENT) | K001 | | |
| | (OUTPATIENT) | K001-001 | | |

(612) (6120)

[ NEXT >> ] — 613
[ << BACK ] — 614

FIG.12B

PATIENT INFORMATION CONFIRMATION — 615

PROTOCOL NAME: MEDICINE ABC
616 — INSTITUTION NAME: ABC HOSPITAL

| PATIENT NAME | FUJI, TARO |
|---|---|
| GENDER | MALE |
| BIRTH DATE | HEISEI12YY1MM1DD |
| CHART (INPATIENT) | K001 |
| NO. (OUTPATIENT) | K001-001 |

617, 618

619 — PATIENT HAVING THE SAME GENDER AND BIRTH DATE IS REGISTERED.
AFTER CONFIRMING IT IS TO REGISTER, PLEASE PRESS "NEXT"

| PATIENT NAME GENDER | BIRTHDAY CASE REGISTRATION NO. | CHART(INPATIENT) CHART(OUTPATIENT) | ADMINISTRATION START DATE ADMINISTRATION END DATE |
|---|---|---|---|
| FT MALE | HEISEI12YY1MM1DD 00073 | K001 K001-001 | |

620

[ NEXT >> ] — 621
[ << BACK ] — 622

| | MALE | FEMALE | UNKNOWN |
|---|---|---|---|
| UNDER 3 YEARS OLD | 👶 | | |
| UNDER 15 YEARS OLD | 🧒 | 👧 | |
| UNDER 35 YEARS OLD | 👨 | 👩 | 🙂 |
| UNDER 64 YEARS OLD | 👨‍🦳 | 👩‍🦳 | |
| OVER 65 YEARS OLD | 👴 | 👵 | |

FIG.13

SURVEY FORM INFORMATION INPUT

PROTOCOL : MEDICINE ABC    INSTITUTION : ABC HOSPITAL

| CASE NO. | RCH00100020001 | INITIALS | TF | GENDER | MALE | BIRTH DATE | HEISEI12Y1M1D | CHART NO. | (INPATIENT) | K001 | OUTPATIENT | K001-001 |
| SURVEY FORM NAME | SURVEY FORM 1 | STATUS | NOT SENT |
| PAGE SELECTION | PATIENT BACKGROUND | ▼ SCREEN SWITCH | | <<BACK | HELP OF SURVEY FORM INPUT SCREEN |

MEDICINE ABC USAGE RESULT SURVEY (1) SURVEY FORM

[PATIENT BACKGROUND]

PLEASE FILL OUT ALL ITEMS FOR A CASE ADVERSE EFFECTS MANIFESTED

| PATIENT INITIALS | NAME TF | GENDER | ○ 1.M  ● 2.F | IF "2.F" PREGNANCY □1.N 2.Y PREGNANCY □ WEEKS | BIRTH DATE | 12 YY  1 MM  1 DD |
| CHAT NO. | INPATIENT K001  OUTPATIENT K001-001 | | | | MEDICAL EXAMINATION STATE (UNDER ADMINISTRATION) | ○ 1:INPATIENT  ○ 2:OUTPATIENT  ● 3:INPATIENT/OUTPATIENT | ○ 1:MEIJI  ○ 2:TAISHO  ○ 3:SHOWA  ○ 4:HEISEI |
| REASON FOR USE | ○ 1.PNEUMOCYSTIS CARINII PHNUMONA CONFIRMED  ○ 2.PNEUMOCYSTIS CARINII PHNUMONA QUESTIONABLE  DIAGNOSTIC NAME WHEN CONFIRMED  ○ 3.OTHERS( ) | | | | DISEASE FACTOR (BASIC DISEASE) | ○ 1.AIDS  ○ 2.MARROW TRANSPLANTATION  ● 3.KIDNEY TRANSPLANTATION  ○ 4.BLOOD DISEASE  ○ 5.OTHERS  ○ 6.UNKNOWN | WEIGHT (AT START OF ADMINISTRATION) ___ kg  IF "2.KIDNEY TRANS", OR "3.MARROW TRANS".  TRANS DATE:  DISEASE NAME:  IF "4.BLOOD DISEASE"  □ 1.LEUCAEMIA  □ 2.HODGKIN'S DISEASE  □ 3.OTHERS ( )  DISEASE NAME IF 5.OTHERS |
| INFECTED TERM | □ MONTHS  □ DAYS  □ UNKNOWN |
| SERIOUSNESS DEGREE | ● 1.MILD  ○ 2.NOT SERIOUS  ○ 3.SERIOUS  ○ 4.OTHERS( ) | | | | COMPLICATION | ● 1.N  ○ 2.Y  ○ 3.UNKNOWN | DISEASE NAME IF "2.Y" |
| IDIOSYNCRASY | ● 1.N  ○ 2.Y  ○ 3.UNKNOWN  ALLERGEN IF "2.Y" | | | | ANAMNESIS | 1.N  ○ 2.Y  ○ 3.UNKNOWN | DISEASE NAME IF "2.Y" |

SAVE

FIG.15A

| PAGE SELECTION | MEDICAL TREATMENT PROGRESS | ▼ | SCREEN SWITCH |
|---|---|---|---|
| | PATIENT BACKGROUND | | |
| | TREATMENT PROGRESS | | |
| | CLINICAL PROGRESS | | |
| | CLINICAL LABORATORY VALUE | | |
| | ADVERSE EVENTS 1 | | |
| | ADVERSE EVENTS 2 | | |
| | ADVERSE EVENTS 3 | | |
| | COMMENT ABOUT ADVERSE EVENTS | | |

SURVEY FORM INFORMATION INPUT    □ ⊡ ☒

PROTOCOL : MEDICINE ABC    INSTITUTION : ABC HOSPITAL

| CASE NO. | RCH0010020001 | INITIALS | TF | GENDER | MALE | BIRTH DATE | HEISEI12Y1M1D | CHART NO. | (INPATIENT) | K001 | OUTPATIENT | K001-001 |
| SURVEY FORM NAME | SURVEY FORM 1 | STATUS | NOT SENT | | | | | | | | | |
| PAGE SELECTION | PATIENT BACKGROUND | ▼ | SCREEN SWITCH | | | | ≪BACK | | HELP OF SURVEY FORM INPUT SCREEN | | | |

630

COMBINATION THERAPY DURING ADMINISTRATION    ○1:N ●2:Y

CHECK IF "2:Y" ↓

□ 1:RADIATION    ☑ 2:BLOOD TRANSFUSION    □ 4:ANESTHESIA    □ 5:DIALYSIS

□ 6:PHYSICAL-ERGO THIONEINE    □ 7:DIET INFORMATION    □ 8:OTHERS (     )

[SAVE]

SURVEY FORM INFORMATION INPUT

| PROTOCOL : MEDICINE ABC | | INSTITUTION : ABC HOSPITAL | | | | | |
|---|---|---|---|---|---|---|---|
| CASE NO. | INITIALS | TF | GENDER | BIRTH DATE | CHART NO. | (INPATIENT) | (OUTPATIENT) |
| RCH0010002001 | ABC | | MALE | HEISEI12Y1M1D | | K001 | K001-001 |
| SURVEY FORM NAME | SURVEY FORM 1 | STATUS | NOT SENT | | | | |
| PAGE SELECTION | PATIENT BACKGROUND ▼ | SCREEN SWITCH | | <<BACK | HELP OF SURVEY FORM INPUT SCREEN | | |

IF SERIOUSNESS DEGREE OF EACH HARMFUL EVENT IS "SERIOUS", REFER TO "SERIOUSNESS DEFINITION" AND CHECK ANY ONE OF I-VII

ADVERSE EVENT NAME 2

| | | | EXPRESSION DATE(yyyy/mm/dd) | GRADE |
|---|---|---|---|---|
| | | | 2000/10/12 | MODERATE ▼ |

| TREATMENT | | OUTCOME | SURVEYD MEDICINE | CAUSAL RELATIONSHIP POSSIBLE FACTOR OTHER THAN SURVEYED MEDICINE | GRAVITY |
|---|---|---|---|---|---|
| SURVEYD MEDICINE | OTHERS | | | | |
| ☐1.CONTINUE ☐2.REDUCE ☐3.PAUSE ☑4.TERMINATE ☐5.OTHERS ( ) | ☐0:NONE ☑1:REMEDY ([PRUG C01]) ☐2:OTHERS ( ) | DATE[2000/01/01] yyyy/mm/dd ☐1:RECOVERY ☑2:REMISSION ☐3:NOT RECOVERED ☐4:SEQUELA ( ) ☐5:DEATH DUE TO THIS HARMFULL EVENT DEATH DATE: (yyyy/mm/dd) (☐AM ☐PM (hh:mm)) ☐9:UNKNOWN | ☐1:YES ☐2:NATBE ☑3:CANNOT DENY ☐4:MERE ☐9:UNKNOWN ☐0:NONE | ☑1.NO ☐ 2.YES 2.IF YES 1.BY COMBINATION MEDICINE ( ) ☐2.BY PRIMARY DISEASE COMPLICATION ☐3.BY COMBINATION THERAPY ☐4.OTHERS ( ) | ☑1.NOT GRAVE ☐1.MINOR ☑2.NOT MINOR ☐2.GRAVE ☐☐☐ .0000 ☐☐☐ .0000 ☐☐☐ .0000 ☐☐☐ .0000 |

SURVEY FORM INFORMATION INPUT

PROTOCOL : MEDICINE ABC        INSTITUTION : ABC HOSPITAL

| CASE NO. | RCH00100020001 | INITIALS | TF | GENDER | MALE | BIRTH DATE | HEISEI12Y1M1D | CHART NO. | (INPATIENT) | K001 | OUTPATIENT | K001-001 |

SURVEY FORM NAME : SURVEY FORM 1   STATUS : NOT SENT

PAGE SELECTION : PATIENT BACKGROUND ▼ SCREEN SWITCH       <<BACK    HELP OF SURVEY FORM INPUT SCREEN

[SERIOUS ADVERSE DRUG REACTION] : ANAPLASTIC ANEMIA, MEGALOBLASTIC ANEMIA, AGRANULOSIS, HEMOLYTIC ANEMIA, PANCYTOPENIA, SHOCK MUCO-CUTANEO-OCULAR SYNDROME(STEVENS-JOHNSON SYNDOROME), TOXIC EPIDERMAL (LYELL SYNDROME),
[OTHER ADVERSE DRUG REACTIONS] :

BLOOD : THROMBOCYTOPENIA, GRANULOCYTOPENIA     KIDNEY : RENAL DAMAGE (BUN ELEVATION, SERUM CREATINE ELEVATION, HEMATURIA)

ANAPHYLAXIS : ERUPTION, ERYTHEMA, BULLOUS, URTICARIA     PSYCHONEURO SYSTEM : HALLUCINATION, PARALYSIS, DEPRESSION, IRRITATION

DIGESTIVE ORGANS : VOMITING, ANOREXIA, NAUSEA     ELECTROLYTE ABNORMALITY : HYPERKALEMIA, HYPONATREMIA

LIVER : GOT ELEVATION, GPT ELEVATION     OTHERS : PHLEBITIS, FEVER, FEELING OF HEAT, PRESSURE INCREASE

SAVE 630, 634, 640

FIG.17A

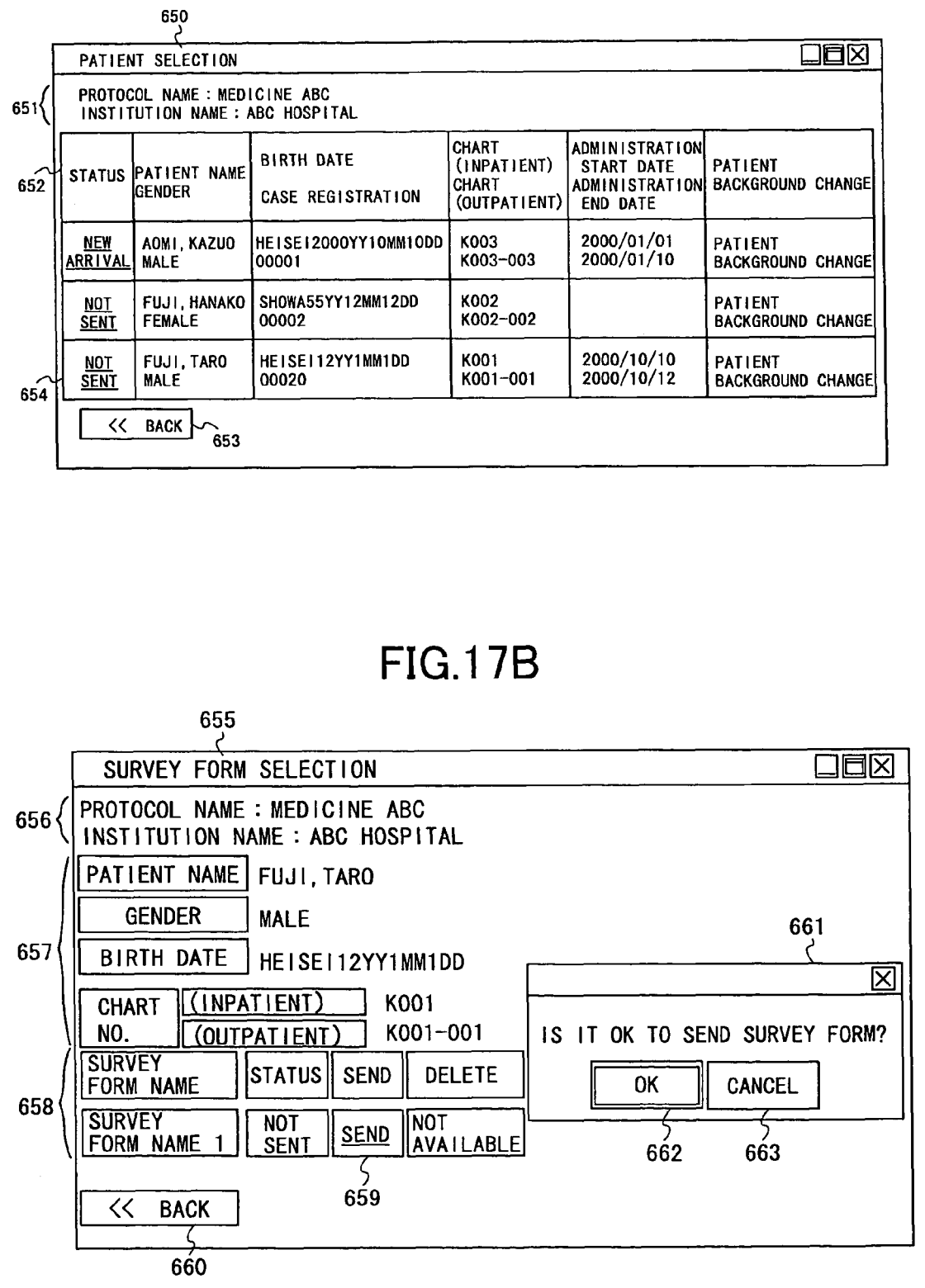

650 PATIENT SELECTION

651 {
PROTOCOL NAME : MEDICINE ABC
INSTITUTION NAME : ABC HOSPITAL

| STATUS | PATIENT NAME GENDER | BIRTH DATE CASE REGISTRATION | CHART (INPATIENT) CHART (OUTPATIENT) | ADMINISTRATION START DATE ADMINISTRATION END DATE | PATIENT BACKGROUND CHANGE |
|---|---|---|---|---|---|
| NEW ARRIVAL | AOMI, KAZUO MALE | HEISEI2000YY10MM10DD 00001 | K003 K003-003 | 2000/01/01 2000/01/10 | PATIENT BACKGROUND CHANGE |
| NOT SENT | FUJI, HANAKO FEMALE | SHOWA55YY12MM12DD 00002 | K002 K002-002 | | PATIENT BACKGROUND CHANGE |
| NOT SENT | FUJI, TARO MALE | HEISEI12YY1MM1DD 00020 | K001 K001-001 | 2000/10/10 2000/10/12 | PATIENT BACKGROUND CHANGE |

652, 654

<< BACK  653

FIG.17B

655 SURVEY FORM SELECTION

656 {
PROTOCOL NAME : MEDICINE ABC
INSTITUTION NAME : ABC HOSPITAL

657 {
| PATIENT NAME | FUJI, TARO |
| GENDER | MALE |
| BIRTH DATE | HEISEI12YY1MM1DD |
| CHART NO. (INPATIENT) | K001 |
| (OUTPATIENT) | K001-001 |

658 {
| SURVEY FORM NAME | STATUS | SEND | DELETE |
|---|---|---|---|
| SURVEY FORM NAME 1 | NOT SENT | SEND | NOT AVAILABLE |

659

<< BACK  660

661 IS IT OK TO SEND SURVEY FORM?

[ OK ]  [ CANCEL ]
 662     663

FIG.18

665 — DEAR ○○○○,

666 — URGENT EVENT OR PREGNANCY CASE IS INCLUDED.

667 — INSTITUTION NAME : ○○HOSIPITAL ○○SECTION

668 — CASE LIST (CASE REGISTRATION NO. -DIVISIONAL NO., PATIENT INITIALS, BIRTH DATE, GENDER, TYPE)
AT001-001,T.A, SHOWA36YY10MM10DD, MALE, ADVERSE EVENTS
AT002-001,D.H, SHOWA32YY05MM12DD, MALE, ADVERSE EVENTS/PREGNANCY
AT005-001,S.K, SHOWA56YY01MM06DD, MALE, ADVERSE EVENTS
AT006-001,N.A, SHOWA41YY12MM01DD, MALE, PREGNANCY

SURVEY FORM SELECTION — 700

PROTOCOL NAME : MEDICINE ABC

| SURVEY REQUEST INSTITUTION NO. | 0000000001 | INSTITUTION NAME | ABC HOSPITAL | SECTION NAME | PHYSICIAN | DOCTOR NAME | IYAMA, SHIRO |

CONTRACT TERM: 2000/10/10–2001/10/10 ~672

RE-SURVEY REQUEST ~673

RE-SURVEY REMINDER

CONTRACT CASE: 150

BACK ~674

671

| STATUS | SURVEY FORM | SURVEY FORM | LOGIC CHECK | INITIALS GENDER | BIRTH DATE CASE REGISTRATION NO. | SURVEY FORM NAME |
|---|---|---|---|---|---|---|
| NEW ARRIVAL | | | LOGIC CHECK | KK MALE | HEISEI2000YY10MM10DD 00001 | SURVEY FORM NAME 1 | SURVEY FORM COMPLETED DATE |

LOGIC CHECK RESULT ~710

LOGIC CHECK COMPLETED.
3 ERRORS ARE FOUND.
PLEASE CONFIRM AT SURVEY FORM
INFORMATION SCREEN.

BACK ~711

FIG.20

SURVEY FORM INFORMATION

PROTOCOL : MEDICINE ABC    INSTITUTION : ABC HOSPITAL

731 — CASE NO. RCH00100001005 INITIALS KK GENDER MALE BIRTH DATE HEISEI2000YY2MM1DD CHART NO. (INPATIENT) K005 (OUTPATIENT) K005-001

732 — SURVEY FORM NAME SURVEY FORM 1 STATUS COMFIRMING

733 — PAGE SELECTION PATIENT BACKGROUND ▽ SCREEN SWITCH — 735

734 — FOR RE-SURVEY    <<BACK  736    HELP OF SURVEY FORM INPUT SCREEN — 737

741

MEDICINE ABC USAGE RESULT SURVEY (1) SURVEY FORM
[PATIENT BACK GROUND]
PLEASE FILL OUT ALL ITEMS FOR A CASE ADVERSE EFFECTS MANIFESTED

| PATIENT INITIALS | NAME KK GENDER | ⦿ 1. MALE  ○ 2. FEMALE | IF "2.F" PREGNANCY □ 1. N □ 2. Y PREGNANCY [ ] WEEKS 748 | BIRTH DATE | ○ 1. MEIJI  ○ 2. TAISHO  ○ 3. SHOWA  ⦿ 4. HEISEI | 745 12 YY 9 MM 10 DD |
|---|---|---|---|---|---|---|
| PATIENT INITIALS | INPATIENT : aaa  OUTPATIENT : bbb | | | MEDICAL EXAMINATION STATE (UNDER ADMINISTRATION) | 1. INPATIENT  2. OUTPATIENT  3. INPATIENT · OUTPATIENT | WEIGHT (AT START OF ADMINISTRATION) 60 kg |
| 744 | ⦿ 1. PNEUMOCYSTIS CARINI PHEUMONA CONFIRMED  ○ 2. PNEUMOCYSTIS CARINI PHEUMONA QUESTIONABLE | | | DISEASE FACTOR (BASIC DISEASE) | ⦿ 1. AIDS  ○ 2. MARROW TRANSPLANTATION  ○ 3. KIDNEY TRANSPLANTATION 746 | IF "2. KIDNEY TRANS." OR "3. MARROW TRANS." TRANS. DATE : DISEASE NAME : IF "4. BLOOD DISEASE" □ 1. LEUCAEMIA □ 2. HODGKIN'S DISEASE □ 3. OTHERS ( ) |
| REASON FOR USE | DIAGNOSTIC NAME WHEN CONFIRMED [ ▽ ] | | | SINGLE SELECTION | | |

CONFIRMATION CONTENTS ☒

750

SUBJECT ITEMS

751 {
| ITEM NAME |
|---|
| BIRTH DATE- ERA |
| BIRTH DATE- YEAR |
| BIRTH DATE- MONTH |
| BIRTH DATE- DAY |

LOGIC CHECK ERROR (THIS REPLY:THE SECOND RE-SURVEY REPLY)

752 {
| COMFIRM | ERROR CODE | ERROR MESSAGE | DATA |
|---|---|---|---|
| ☑ | RCH001_E00022 | DATE AFTER "START DATE OF MEDICINE ABC" | 20000101 |

7520

REQUEST CONTENTS

753 {
Please correct input data.
The birth date shows
after administration date.

754 ~ [SAVE] [CLOSE] ~755

LOGIC CHECK ERROR (PREVIOUS REPLY:FIRST RE-SURVEY REPLY)

756 {
| ERROR CODE | ERROR MESSAGE | DATA |
|---|---|---|
| RCH001_E00022 | DATE AFTER "START DATE OF MEDICINE ABC" | 20000101 |

PREVIOUS REQUEST DONTENTS :

757 { Please modify.

758, 759 bracket the right side

STORING PROCESS CONFIRMATION ☒

LOGICK CHECK CONTENTS

761 {
| ERROR CODE | ERROR MESSAGE |
|---|---|
| RCH001_E00022 | DATE AFTER "START DATE OF MEDICINE ABC" |

REQUEST CONTENTS

762 {
Please correct input data.
The birth date shows
after administration date.

[CLOSE] ~763

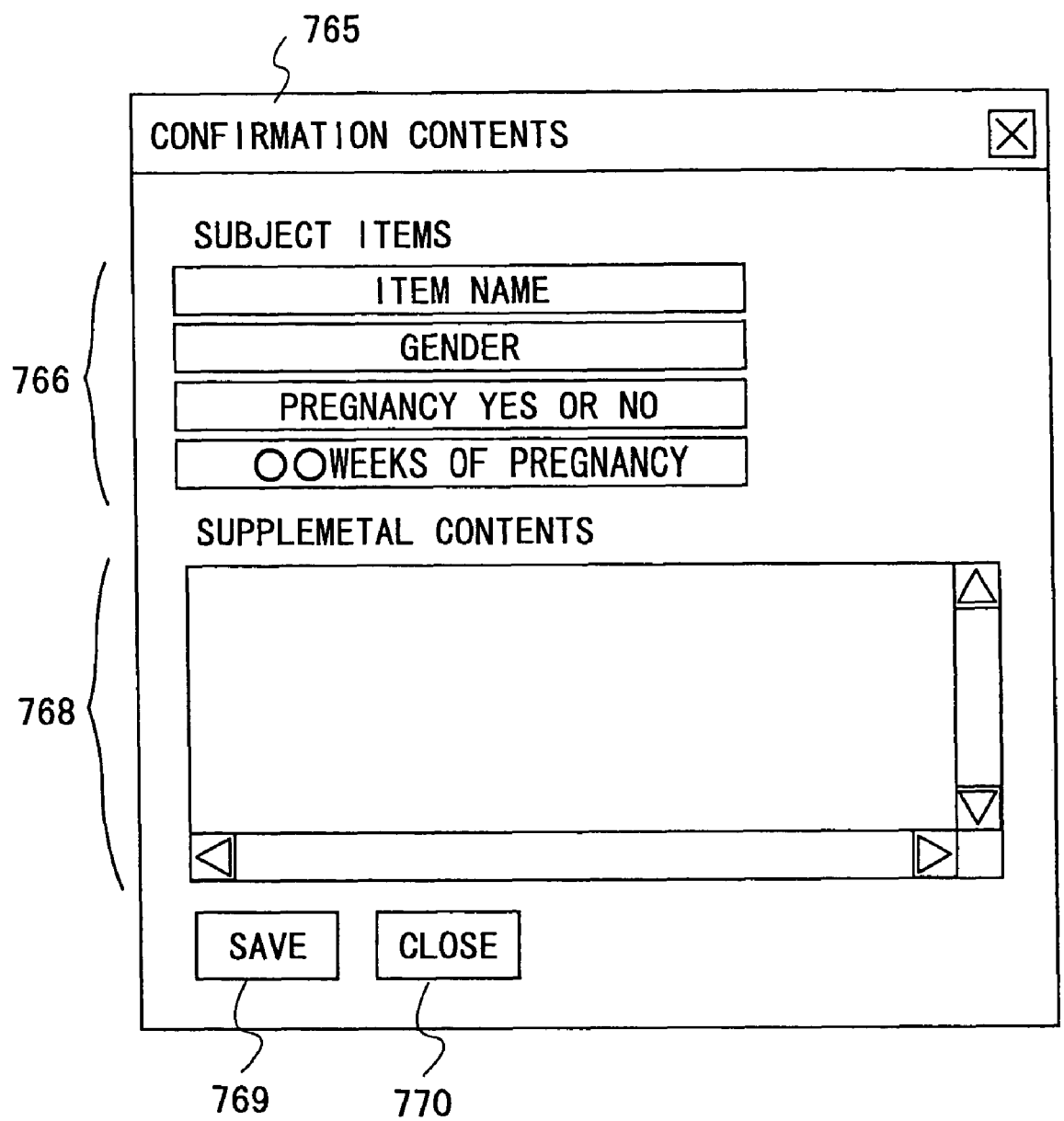

FIG.23A

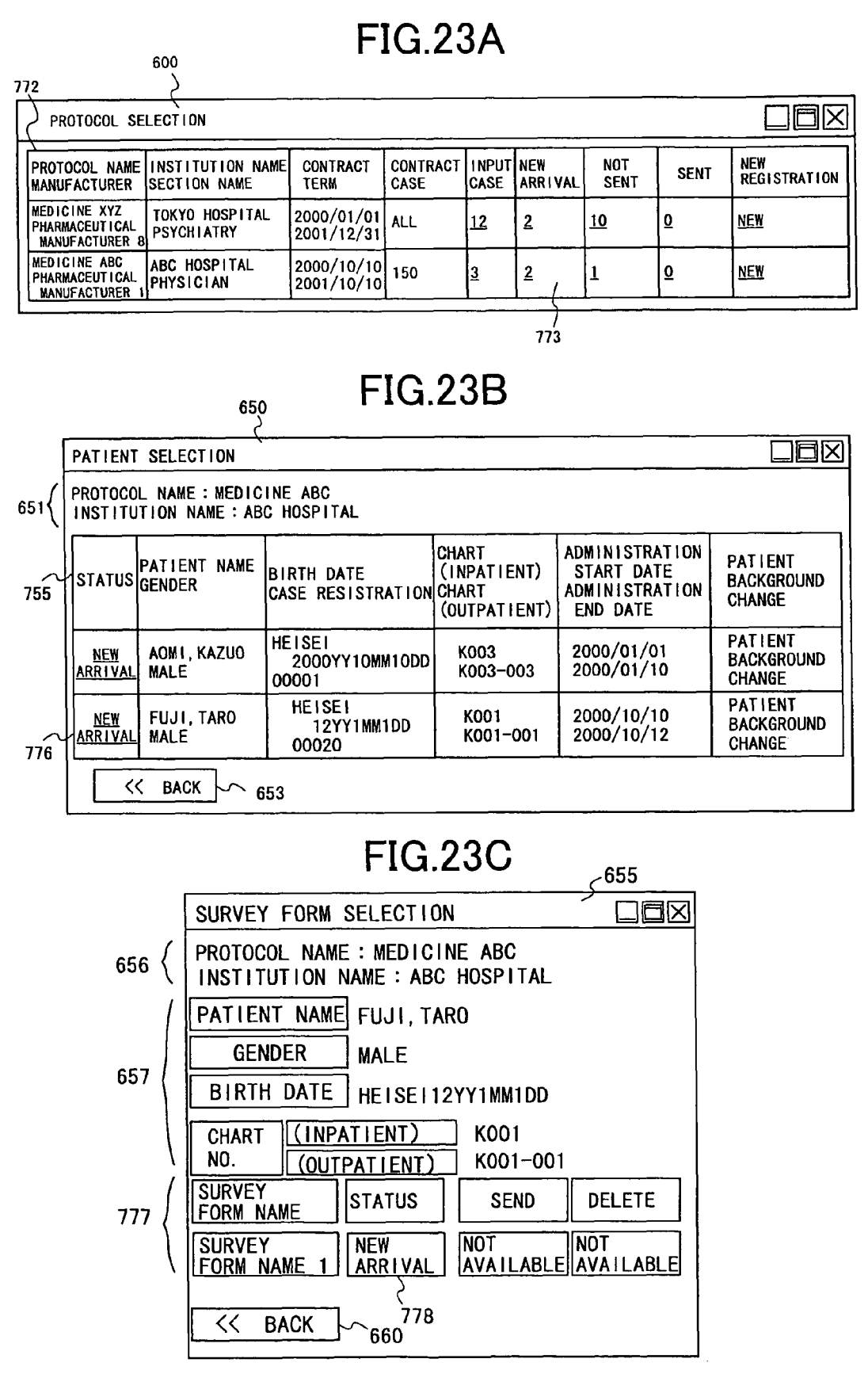

PROTOCOL SELECTION

| PROTOCOL NAME MANUFACTURER | INSTITUTION NAME SECTION NAME | CONTRACT TERM | CONTRACT CASE | INPUT CASE | NEW ARRIVAL | NOT SENT | SENT | NEW REGISTRATION |
|---|---|---|---|---|---|---|---|---|
| MEDICINE XYZ PHARMACEUTICAL MANUFACTURER 8 | TOKYO HOSPITAL PSYCHIATRY | 2000/01/01 2001/12/31 | ALL | 12 | 2 | 10 | 0 | NEW |
| MEDICINE ABC PHARMACEUTICAL MANUFACTURER 1 | ABC HOSPITAL PHYSICIAN | 2000/10/10 2001/10/10 | 150 | 3 | 2 | 1 | 0 | NEW |

FIG.23B

PATIENT SELECTION

PROTOCOL NAME : MEDICINE ABC
INSTITUTION NAME : ABC HOSPITAL

| STATUS | PATIENT NAME GENDER | BIRTH DATE CASE RESISTRATION | CHART (INPATIENT) CHART (OUTPATIENT) | ADMINISTRATION START DATE ADMINISTRATION END DATE | PATIENT BACKGROUND CHANGE |
|---|---|---|---|---|---|
| NEW ARRIVAL | AOMI, KAZUO MALE | HEISEI 2000YY10MM10DD 00001 | K003 K003-003 | 2000/01/01 2000/01/10 | PATIENT BACKGROUND CHANGE |
| NEW ARRIVAL | FUJI, TARO MALE | HEISEI 12YY1MM1DD 00020 | K001 K001-001 | 2000/10/10 2000/10/12 | PATIENT BACKGROUND CHANGE |

<< BACK

FIG.23C

SURVEY FORM SELECTION

PROTOCOL NAME : MEDICINE ABC
INSTITUTION NAME : ABC HOSPITAL

| PATIENT NAME | FUJI, TARO |
|---|---|
| GENDER | MALE |
| BIRTH DATE | HEISEI12YY1MM1DD |
| CHART NO. | (INPATIENT) K001 |
| | (OUTPATIENT) K001-001 |

| SURVEY FORM NAME | STATUS | SEND | DELETE |
|---|---|---|---|
| SURVEY FORM NAME 1 | NEW ARRIVAL | NOT AVAILABLE | NOT AVAILABLE |

<< BACK

655 SURVEY FORM SELECTION

656 PROTOCOL NAME : MEDICINE ABC
INSTITUTION NAME : ABC HOSPITAL

657
- PATIENT NAME | FUJI, TARO
- GENDER | MALE
- BIRTH DATE | HEISEI12YY1MM1DD
- CHART NO. | (INPATIENT) K001 / (OUTPATIENT) K001-001

788

| SURVEY FORM NAME | STATUS | SEND | DELETE |
|---|---|---|---|
| SURVEY FORM NAME 1 | NOT SENT | SEND | NOT AVAILABLE |

789

661 IS IT OK TO SEND SURVEY FORM?
[OK] 662  [CANCEL] 663

<< BACK  660

FIG.25B

655 SURVEY FORM SELECTION

656 PROTOCOL NAME : MEDICINE ABC
INSTITUTION NAME : ABC HOSPITAL

657
- PATIENT NAME | FUJI, TARO
- GENDER | MALE
- BIRTH DATE | HEISEI12YY1MM1DD
- CHART NO. | (INPATIENT) K001 / (OUTPATIENT) K001-001

788

| SURVEY FORM NAME | STATUS | SEND | DELETE |
|---|---|---|---|
| SURVEY FORM NAME 1 | SENT | NOT AVAILABLE | NOT AVAILABLE |

<< BACK

SURVEY FORM IS SENT  790

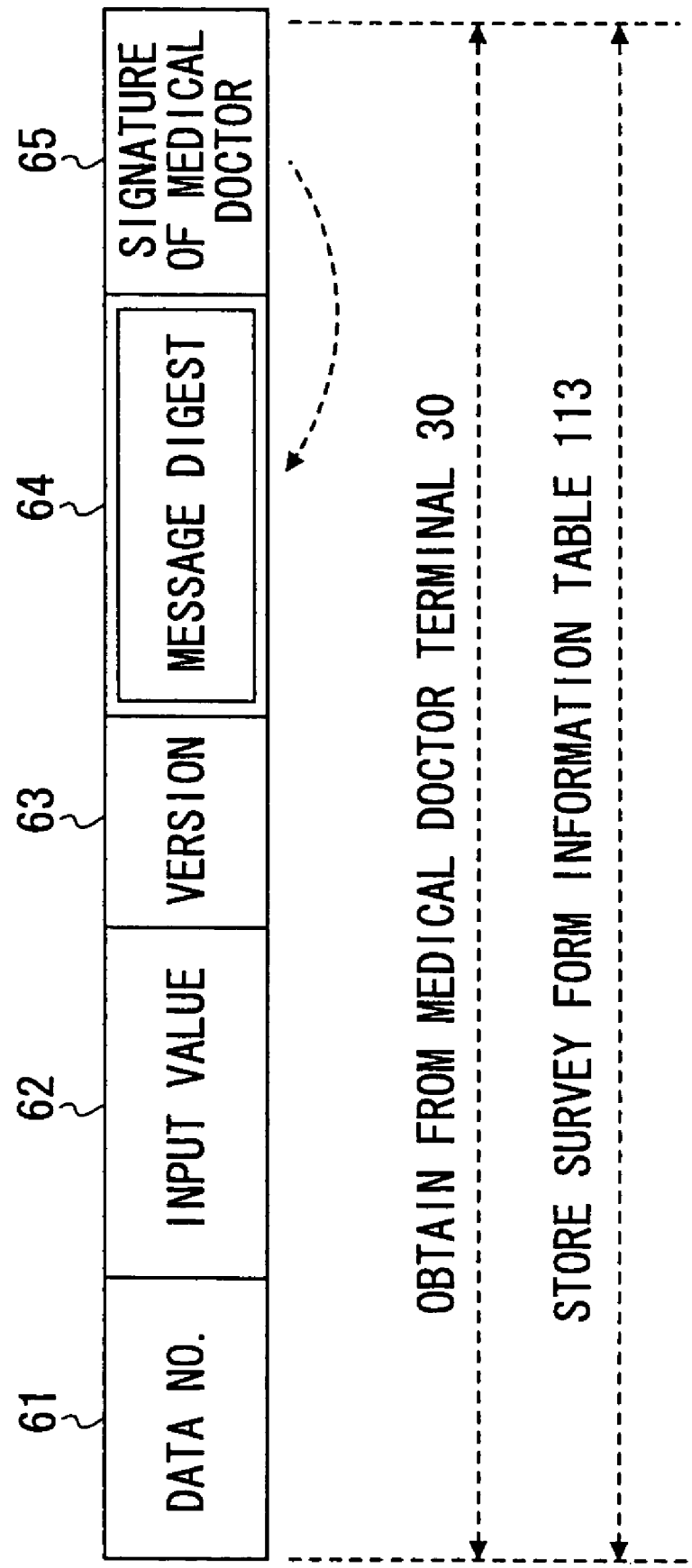

DATA VERIFICATION PROGRESS MANAGING AND SUPPORTING SERVER

TECHNICAL FIELD

The present invention relates to a data verification supporting server and a data verification supporting method for supporting verification of data that is inputted to each item of a survey form for surveying an effect of implementing a product.

Moreover, the present invention relates to an electronic signature client for conducting an electronic signature to the survey form provided by the data verification supporting server.

Furthermore, the present invention relates to a data verification supporting system for supporting verification of data that is inputted to each item of a survey form for surveying an effect of implementing a product.

Moreover, the present invention relates to an information managing server and an information managing method for providing private information concerning a person after converting a person name into initials.

BACKGROUND ART

Conventionally, in the pharmaceutical industry, in order to guarantee safety and effectiveness of a medicine, post-marketing surveillance is conducted for a medicine being marketed. For the post-marketing surveillance, a contact person from a pharmaceutical manufacturer visits a doctor and makes requests for surveillance and trials of the medicine. The doctor fills out a predetermined survey form, which the contact person gave to the doctor, for each prescription case and signs on or affixes his seal to the predetermined survey form. Then, the predetermined survey form is provided to the pharmaceutical manufacturer from the doctor through a form collector. That is, in procedures for the post-marketing surveillance, generally, the doctor transcribes conditions of patients, for whom the doctor prescribed the medicine that the pharmaceutical manufacturer requested information about, from clinical charts to the survey forms. Then, the pharmaceutical manufacturer inputs information transcribed on the survey forms into a DB (database). The pharmaceutical manufacturer obtains statistics based on data inputted into the DB, analyzes the statistics and then reports a result of the post-marketing surveillance to the Ministry of Health and Welfare.

After that, the pharmaceutical manufacturer maintains and manages the survey forms signed or sealed by the doctor to ensure that the reported result is based on the survey forms from the doctor.

By conducting the above procedures, the safety and effectiveness of the medicine is guaranteed.

However, the above conventional procedures for the post-marketing surveillance have disadvantages as follows:

In order to report an accurate result to the Ministry of Health and Welfare, for example, when data are inputted from the survey forms to the DB in the pharmaceutical manufacturer, several persons separately input the same data to the DB. After that, the data inputted by each person in the DB is compared with each other and is reconfirmed to prevent mistakes of inputting data so as to improve accuracy of input data. In general, since the pharmaceutical manufacturer is under an obligation to survey more than a given number of cases, for example 3,000 cases, for one medicine, a large amount of time and labor power are required to verify consistency between data inputted by the several persons. However, it is still difficult to obtain accurate input data consistent with the data filled out by the doctor on the survey form.

Moreover, in a transcription from the clinical chart to the survey form by the doctor, for protection of a patient's privacy, it is required that the patient's name not be filled out on the survey form. Instead, an initial name is written on the survey form to specify that patient. After the consistency of the data inputted to the DB by the several persons of the pharmaceutical manufacturer is verified, a program is used to check for a logical conflict of the data. When the program finds the logical conflict in the survey form, the contact person of the pharmaceutical manufacturer visits and requests the doctor for the survey again by a request letter in which the contact person has made a comment for each logical conflict in the survey form to the doctor. Similarly, the above procedures are conducted again for the survey form provided from the doctor in response to the request. The procedures are repeated each time the survey is conducted until the survey form does not have any logical conflicts. When the credibility of the survey form is verified by repeating the survey, the data from the survey form is fixed. Therefore, the data becomes available to be analyzed by the pharmaceutical manufacturer and then the pharmaceutical manufacturer can report the analysis result to the Ministry of Health and Welfare.

In the conventional procedures for post-marketing surveillance, a considerable amount of labor and time of the doctor and the pharmaceutical manufacturer is consumed until the credibility of the data of the survey form is verified. Also, since the patient's name in the survey form to specify the patient is transcribed by the initial name by the doctor, the doctor has to find the clinical chart of that patient when the doctor is requested for the survey again. Thus, it is an inconvenience for the doctor. In other surveillance conducted by the pharmaceutical manufacturer, similar problems to the above procedures of post-marketing surveillance occur.

DISCLOSURE OF INVENTION

Therefore, it is a first object of the present invention to provide a data verification supporting server and a data verification supporting method for supporting verification of data that is inputted to each item of a survey form for surveying an effect of implementing a product.

Also, it is a second object of the present invention to provide an information management server and an information management method for converting a person name into an initial name and then providing private information related to a person.

In order to achieve the first object, the present invention, which is a data verification supporting server for supporting verification of data which is inputted to each item of a survey form for surveying an effect of implementing a product, is arranged to include a survey form managing part managing the survey form sent from an implementer terminal of an implementer, with version information showing a revised number of the survey form; a re-survey information managing part informing the implementer of a re-survey inquiry based on a re-survey inquiry request for requesting a re-survey, which is received from a verifier terminal of a verifier verifying the survey form, the re-survey inquiry request indicating the implementer who sent the survey form; and a survey form maintaining part maintaining the survey form and the version information managed by the survey form managing part when notification of a verification completion of the survey form is received from the verifier terminal.

In this data verification supporting server, during the term in which the re-survey is required to the survey form sent by the implementer, it is possible to repeat requesting the re-survey with respect to the implementer. And the completed survey form is stored with a version number.

Accordingly, the verifier is not required to visit to the implementer for many times until the survey form is completed, and it is not required to input data of the survey form by a plurality of persons. Moreover, since the completed survey form is stored with the version number, a version management can be automatically conducted. Furthermore, since a manager of the data verification supporting server can be separated from the implementer and the verifier, it is possible to guarantee reliability of information of the survey form.

Moreover, since the data verification supporting server can be arranged so as to conduct an authentication based on authentication information of the implementer attached to the survey form, it is possible to guarantee the reliability of the information of the survey form even if the data verification supporting server is arranged at a verifier side.

For example, the implementation of the product is the survey of the patient to whom the medicine is administrated.

For example, the data verification supporting server is a server that is managed by an ASP service supplier.

For example, the implementer is a medical doctor.

For example, the verifier is a pharmaceutical manufacturer person in charge.

For example, the survey form is a survey form in which a condition of the patient after the medicine is administrated to the patient is entered by the medical doctor and which is used to survey influence of an adverse drug reaction by the medicine.

Moreover, in order to achieve the first object, the present invention, which is data verification supporting method for supporting verification of data which is inputted to each item of a survey form for surveying an effect of implementing a product, is arranged to include a survey form managing step of managing the survey form sent from an implementer terminal of an implementer, with version information showing a revised number of the survey form; a re-survey information managing step of informing the implementer of a re-survey inquiry based on a re-survey inquiry request for requesting a re-survey, which is received from a verifier terminal of a verifier verifying the survey form, the re-survey inquiry request indicating the implementer who sent the survey form; and a survey form maintaining step of maintaining the survey form and the version information managed by the survey form managing step when notification of a verification completion of the survey form is received from the verifier terminal. The reliability of the survey form information collected from the implementer can be guaranteed by the manager of the data verification supporting server.

In order to achieve the second object, the present invention, which is an information managing server for providing private information concerning a person, is arranged to include a display screen providing part providing input screen information that is displayed at a first user terminal of a first user inputting the private information, with an initial converting part activated at the first user terminal and converting a person name inputted by the first user into an initial name; a private information managing part managing the initial name converted by the initial converting part and an encrypted person name when the private information received from the first user terminal is registered; and a display controlling part displaying the initial name as the person name when displaying the private information at a second user terminal of a second user referring to the private information, and displaying a decrypted person name when displaying the private information at the first user terminal.

In this information managing server, a person name is converted into initials when the person name is inputted, at a side of the terminal inputting as the private information. Moreover, when the person information is managed, the private information is managed by an encrypted person name and a converted person name. Furthermore, the private information can be controlled to provide by the person name to the first user who actually inputted the private information while the private information can be controlled to provide by the initials to the second user to whom the private information is provided.

BRIEF DESCRIPTION OF DRAWINGS

Features and advantages of the present invention will become more apparent from reading the following detailed description in conjunction with the accompanying drawings:

FIG. 3 is a diagram showing an example of status transition of the survey form.

FIG. 4 is a diagram showing a hardware configuration.

FIG. 8 is a diagram showing an example of a survey form management screen provided to a pharmaceutical manufacturer terminal.

FIG. 9 is a diagram showing an example of a contractual institution input screen for a pharmaceutical manufacturer to input contractual institution information.

FIG. 11 is a diagram showing an example of a protocol selection screen provided to a medical doctor terminal.

FIG. 12A is a diagram showing an example of a screen for inputting patient information, FIG. 12B is a diagram showing an example of a screen for checking patient information, and FIG. 12C is a diagram showing an example of a portrait table used to manage a portrait corresponding to age and gender.

FIG. 13 is a diagram showing a first example of a survey form information input screen.

FIG. 15A is a diagram showing another example of a page selection, and FIG. 15B is a diagram showing a second example of a survey form information input screen.

FIG. 16A is a diagram showing a third example of a survey form information input screen, and FIG. 16B is a diagram showing a fourth example of a survey form information input screen.

FIG. 17A is a diagram showing an example of a patient selection screen for sending the survey form and FIG. 17B is a diagram showing an example of a survey form selection screen for sending the survey form.

FIG. 18 is a diagram showing an example of e-mail indicating an urgent event occurrence.

FIG. 19A is a diagram showing an example of the survey form selection screen provided to the pharmaceutical manufacturer terminal, and FIG. 19B is a diagram showing an example of a logic check result.

FIG. 20 is a diagram showing an example of a survey form information screen.

FIG. 21A is a diagram showing an example of a check screen of a logic check, and FIG. 21B is a diagram showing an example of a storing process confirmation screen.

FIG. 22 is a diagram showing another example of a confirmation contents screen.

FIG. 23A is a diagram showing an example of a protocol list which the medical doctor in charge surveys at a re-survey, FIG. 23B is a diagram showing an example of a patient selection screen at the re-survey, and FIG. 23C is a diagram showing an example of the survey form selection screen at the re-survey.

FIG. 24 is a diagram showing an example of a re-survey request contents display screen.

FIG. 25A is a diagram showing an example of a screen for sending a re-surveyed survey form, and FIG. 25B is a diagram showing an example of a-screen showing a transmission completion.

FIG. 29 is a diagram showing an example of a data structure of a survey form information record.

BEST MODE FOR CARRYING OUT THE INVENTION

Figure 1:
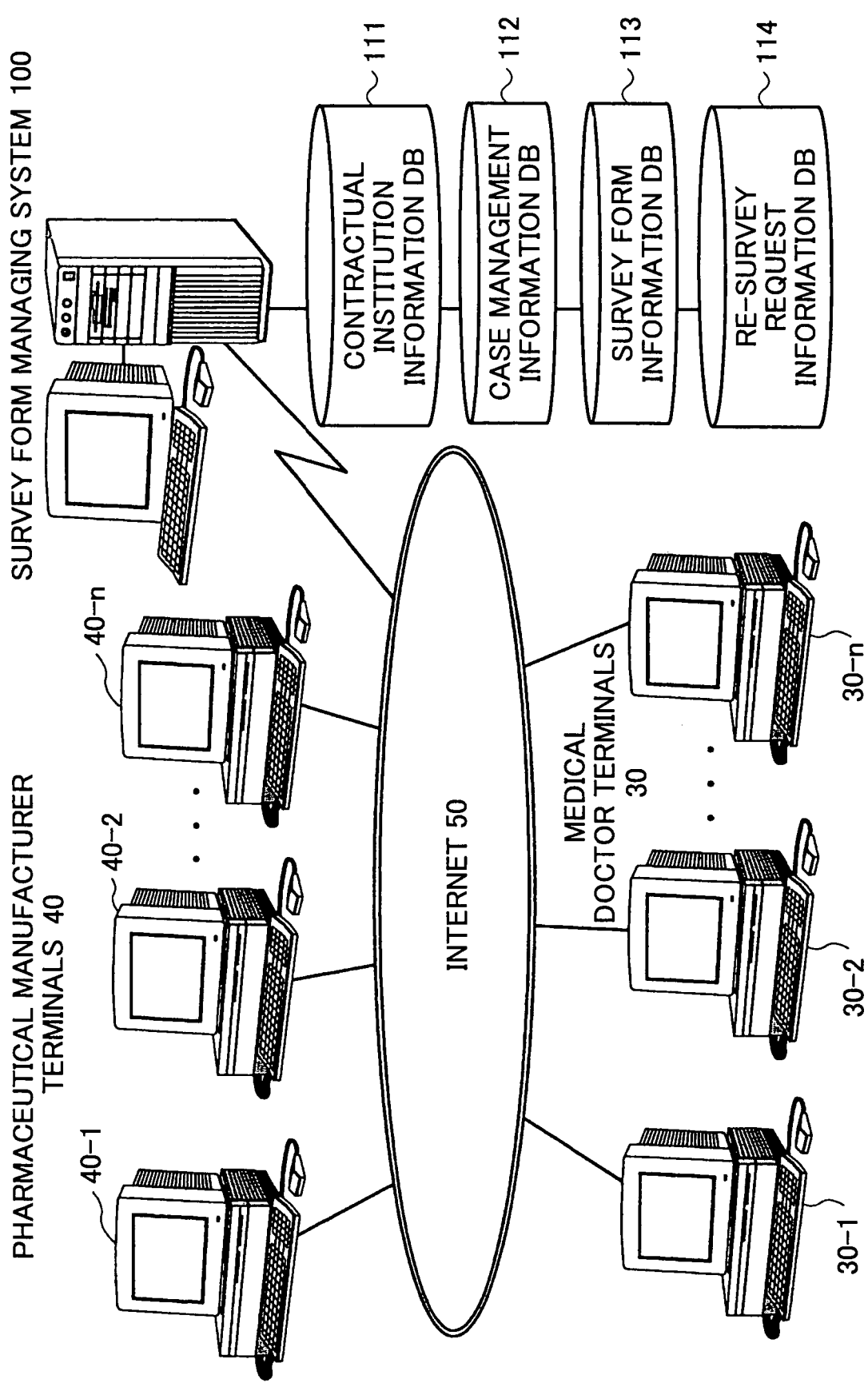
FIG. 1 is a diagram showing a network configuration.

For example, a network forming a survey form managing system to which a data reliability verifying method is applied is shown in FIG. 1, according to an embodiment of the present invention.

As shown in FIG. 1, a survey form managing system 100 includes a contractual institution information DB (data base) 111 that manages contract information contracted by the pharmaceutical manufacturer and a medical doctor, a case management information DB 112 that manages information concerning a patient registered as a case by the medical doctor in charge, a survey form information DB 113 that manages a survey form into which the condition of the patient after prescribing a medicine requested from the pharmaceutical manufacturer is inputted from each of the medical doctor terminals 30 by the medical doctor in charge for each case (each patient), and a re-survey request information DB 114 that manages a re-survey request to the survey form submitted from each of the medical doctor terminals 30. The survey form managing system 100 is mutually connected with each of pharmaceutical manufacturer terminals 40 and each of the medical doctor terminals 30 through the Internet 50.

When the survey form managing system 100 is used from the pharmaceutical manufacturer terminals 40, a pharmaceutical manufacturer person in charge inputs information concerning institutions such as a hospital which contracted to the survey form managing system 100, and information concerning the medical doctor in charge who works in the institution requested to survey, through the Internet 50. The information inputted by the pharmaceutical manufacturer person in charge is stored in the contractual institution information DB 111.

If a pharmaceutical manufacturer person in charge requests a predetermined medical doctor in charge to input into the survey form, from the pharmaceutical manufacturer terminal 40 through the survey form managing system 100, survey request electronic mail requesting survey will be sent to the predetermined medical doctor in charge. In the following, electronic mail is simply called as e-mail.

After receiving the survey request e-mail at the medical doctor terminal 30, the medical doctor in charge inputs information concerning a patient based on a chart of the patient from a patient information input screen for inputting the information concerning the patient provided by the survey form managing system 100. The information concerning the patient is stored in the case management information DB 112 as case information. After that, the medical doctor terminal 30 is allowed to input into a survey form information input screen for inputting the survey for each case provided by the survey form managing system 100. The data inputted into the input screen from the medical doctor terminal 30 are stored in the survey form information DB 113.

Instead of the medical doctor in charge conventionally transferring case data to the survey form (paper form) from the chart, and filling in the survey form, the medical doctor in charge directly inputs data at the patient input screen and the survey form information input screen provided by the survey form managing system 100 to the medical doctor terminal 30. Accordingly, the pharmaceutical manufacturer person in charge does not need to visit the medical doctor in charge, in order to collect survey forms. Moreover, the medical doctor in charge can directly input into the survey form from the medical doctor terminal 30. The data input confirmation workload by several pharmaceutical manufacturer persons in charge can be eliminated. Therefore, workload can be reduced and an accuracy of the information can be improved. That is, a pharmaceutical manufacturer does not need manual operation. Moreover, it becomes possible to obtain data itself as inputted by the medical doctor in charge.

As for the survey form data stored in the survey form information DB 113, contents are verified by a logic check of the survey form managing system 100. Based on a verification result, the pharmaceutical manufacturer person in charge requests a re-survey from the pharmaceutical manufacturer terminal 40 with re-survey request e-mail to the medical doctor in charge.

By repeating the logic check and re-survey request by the survey form managing system 100 several times, logic inconsistency or a like is modified and the survey form is completed. Then, the survey form is maintained using the survey form information DB 113 as fixed data that cannot be changed.

Next, in the network configuration shown in FIG. 1, an operating procedure performed at the pharmaceutical manufacturer terminal 40 and the medical doctor terminal 30 in the case of using the survey form managing system 100 will be described with reference to FIG. 2.

Figure 2:
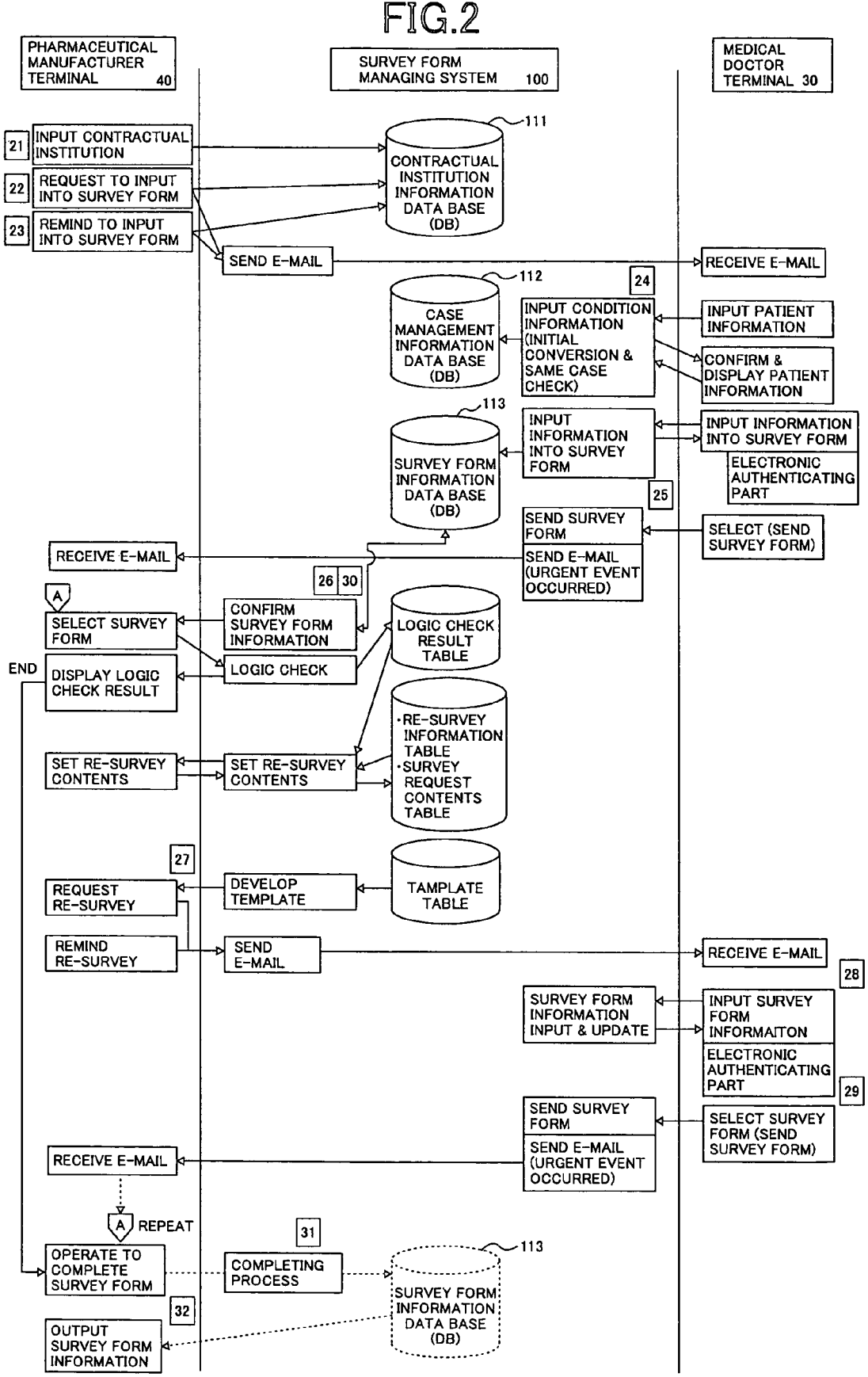
FIG. 2 is a diagram showing an operating procedure in a case of using a survey form managing system.

FIG. 2 is a diagram showing the operating procedure in the case of using the survey form managing system.

In FIG. 2, the pharmaceutical manufacturer person in charge inputs information of the contractual institution and the medical doctor in charge from the pharmaceutical manufacturer terminal 40 (operating procedure 21), and requests the medical doctor in charge to input into the survey form (operating procedure 22). By the operating procedure 22, the survey form managing system 100 enables the medical doctor in charge to input into the survey form and sends predetermined e-mail, which requests the medical doctor to input into the survey form, just like from the pharmaceutical manufacturer terminal 40.

Moreover, in a case in which the medical doctor in charge has not inputted into the survey form for a while after the above-mentioned operating procedure 22, the pharmaceutical manufacturer person in charge can send the predetermined mail which reminds to input into the survey form provided by the survey form managing system 100 to the medical doctor in charge (operating procedure 23).

The medical doctor in charge inputs a case from the patient input screen provided by the survey form managing system 100 at the medical doctor terminal 30 after the survey form input request by the above-mentioned operating procedure 22 or 23 (operating procedure 24). The medical doctor in charge inputs the case with reference to a chart of a patient. In this survey form managing system 100, the medical doctor in charge can input the patient name indicated by the chart in katakana (phonetic word). The initial converting program, which is sent from the survey form managing system 100 to the medical doctor terminal 30, converts a patient name into initials. When the case in which the medical doctor in charge inputted from the medical doctor terminal 30 is registered into the case management information DB 112, the katakana name inputted by the medical doctor is encrypted, the initials of the patient name and an encrypted patient name are stored with this case.

Accordingly, after that, when the survey form managing system 100 provides survey form information, the survey form managing system 100 can display the patient name by a katakana notation to the medical doctor terminal 30 while displaying by an initial notation to the pharmaceutical manufacturer terminal 40. Therefore, at the medical doctor terminal 30, at the re-survey, since the medical doctor in charge can refer to the patient name with full name, the medical doctor can refer to the chart easily. Moreover, the medical doctor in charge and the pharmaceutical manufacturer person in charge can specify the patient to each other when communicating to confirm the survey form or a like.

Moreover, in the above-mentioned operating procedure 24, the survey form managing system 100 checks by searching the case management information DB 112 whether or not the same case information exists. When there is the same case information, the medical doctor terminal 30 is informed that the same case information is already registered. Accordingly, the medical doctor in charge can be prevented from registering an inadequate duplication case.

When the case is registered, that is, when the medical doctor in charge completes to input the patient information, the survey form managing system 100 manages the information concerning the survey form corresponding to the case by survey form management information, and sets "NOT SEND" as a status of the survey form at the medical doctor side and "(blank)" as a status at the pharmaceutical manufacturer side (refer to FIG. 3).

After the medical doctor in charge inputs case information at the medical doctor terminal 30, the medical doctor inputs and updates information for each case from the survey form input screen provided by the survey form managing system 100, and sends the survey form to the pharmaceutical manufacturer person in charge (operating procedure 25). In the operating procedure 25, referring to the item definition of the survey form information DB 113, based on a survey form input screen, the survey form managing system 100 forms a survey form input screen, and provides the survey form input screen to the medical doctor terminal 30. Moreover, the survey form managing system 100 stores the information on the survey form inputted from the medical doctor terminal 30 by the medical doctor in charge as the survey form information in the survey form information DB 113. Furthermore, by an operation of sending e-mail at the medical doctor terminal 30, e-mail indicating that the predetermined survey form is inputted is sent from the medical doctor in charge to the pharmaceutical manufacturer person in charge. And the survey form managing system 100 changes a medical doctor side status of this survey form of the survey form management information into "SENT" and a pharmaceutical manufacturer side status into. "NEW ARRIVAL" (refer to FIG. 3).

Furthermore, in the above-mentioned operating procedure 25, based on the information on the survey form inputted from the medical doctor terminal 30, regarding the requested medicine, when the information indicating an occurrence or a like of an urgent event such as adverse events, a pregnancy case, or a like, that should be immediately responded to, is included, the survey form managing system 100 generates e-mail indicating the urgent event occurrence, and the e-mail is sent from the medical doctor in charge to a pharmaceutical manufacturer person in charge (for example, a person in charge of safety).

The survey form managing system 100 automatically sends the e-mail indicating the urgent event occurrence. Therefore, the medical doctor in charge can save a time and effort to inform the case in which the urgent event independently occurred, to the pharmaceutical manufacturer person in charge. Moreover, the pharmaceutical manufacturer person in charge can receive the e-mail at the pharmaceutical manufacturer terminal 40, when the medical doctor in charge inputs the survey form. Accordingly, the pharmaceutical manufacturer person can promptly respond to report indicating the urgent event occurrence.

After requesting or reminding to input into the survey form from the pharmaceutical manufacturer terminal 40 to the medical doctor in charge in above-mentioned operating procedure 22 or 23, based on survey form management information, with reference to the contractual institution information screen which the survey form managing system 100 provides, the pharmaceutical manufacturer person in charge selects the survey form on which the status is displayed as "NEW ARRIVAL", and checks the information on the survey form (operating procedure 26).

The survey form managing system 100 changes the survey form status at the medical doctor side into "MANUFACTURE RECEIVED" and the survey form status at the pharmaceutical manufacturer side into "CONFIRMING" (refer to FIG. 3).

In the operating procedure 26, when the pharmaceutical manufacturer terminal 40 selects a survey form, the survey form managing system 100 executes the logic check for verifying whether or not the information on a selected survey form has logic inconsistency. And the survey form including an execution result is displayed on the pharmaceutical manufacturer terminal 40.

The pharmaceutical manufacturer person in charge sets the items for which the re-survey by the medical doctor in charge is needed, based on the survey form including the execution result of the displayed logic check. The execution result of the logic check by the survey form managing system 100 and the information concerning the items requiring the re-survey set at the pharmaceutical manufacturer terminal 40 are stored in the re-survey request information DB 114 as re-survey information. Moreover, when the request contents are inputted by the pharmaceutical manufacturer person in charge, among the items set by the pharmaceutical manufacturer person, the request contents are stored in the re-survey request information DB 114 as re-survey request contents.

On the other hand, when the re-survey request to the medical doctor in charge is not needed, the survey form is completed (operating procedure 31).

The pharmaceutical manufacturer person in charge requests the re-survey to the medical doctor in charge (operating procedure 27). By the operation procedure 27 at the pharmaceutical manufacturer terminal 40, the survey form managing system 100 sends a predetermined e-mail requesting a re-survey from the pharmaceutical manufacturer person in charge to each medical doctor. The survey form managing system 100 changes the survey form status at the medical doctor side of the survey form management information into "NEW ARRIVAL" and changes the survey form status at the pharmaceutical manufacturer side into "REQUESTING" (refer to FIG. 3). Moreover, the survey form managing system 100 increments the number of the history versions for the survey form information as survey form history by one, and transmits the survey form information to the survey form history table 134.

After the re-survey request, the pharmaceutical manufacturer person in charge refers to a contractual institution information screen. When the survey form status remains as "REQUESTING", the pharmaceutical manufacturer person reminds the re-survey with respect to the medical doctor in charge (operating procedure 28). The survey form managing system 100 sends a predetermined e-mail reminding the predetermined re-survey from the pharmaceutical manufacturer terminal 40 to the medical doctor in charge, by the above-mentioned operating procedure 28 by the pharmaceutical manufacturer person in charge.

After the medical doctor in charge receives the e-mail requesting or reminding the re-survey from the pharmaceutical manufacturer person in charge at the medical doctor terminal 30, the medical doctor modifies the information on the survey form for the re-survey (operating procedure 28). The survey form managing system 100 changes the survey form status of the medical doctor side into "NOT SEND", and remains the survey form status the pharmaceutical manufacturer side (refer to FIG. 3).

The medical doctor in charge sends the survey form information modified at the medical doctor terminal 30 to the pharmaceutical manufacturer person in charge (operating procedure 29). In response to the above-mentioned operating procedure 29 by the medical doctor in charge, the survey form managing system 100 sends e-mail showing that the predetermined re-survey has been conducted, to the pharmaceutical manufacturer person in charge.

When the pharmaceutical manufacturer person in charge at the pharmaceutical manufacturer terminal 40 receives, from the medical doctor in charge, the e-mail showing that the predetermined re-survey has been conducted, based on the survey form management information, the pharmaceutical manufacturer person in charge refers to the contractual institution information screen provided by the survey form managing system 100, selects the survey form where the status is displayed as the "NEW ARRIVAL", and confirms the information on the survey form (operating procedure 31). The survey form managing system 100 changes the survey form status the medical doctor side into "MANUFACTURE RECEIVED", and changes the survey form status at the pharmaceutical manufacturer side into "CONFIRMING" (refer to FIG. 3).

In the operating procedure 31, when the pharmaceutical manufacturer person in charge selects the survey form, in a manner similar to the above-mentioned operating procedure 26, the survey form managing system 100 executes the logic check for verifying whether or not the information on the selected survey form has logic inconsistency and displays the survey form information including the execution result at the pharmaceutical manufacturer terminal 40. Based on the survey form including the execution result of the displayed logic check, the pharmaceutical manufacturer person in charge sets the items that need the re-survey by the medical doctor in charge and requests the re-survey to the medical doctor in charge in the operating procedure 27, again.

When the request of the re-survey is not needed to the medical doctor in charge, the survey form is completed (operating procedure 31).

In the operating procedure 31, the pharmaceutical manufacturer person in charge confirms the survey form information at the pharmaceutical manufacturer terminal 40. When the request of the re-survey is not needed to the medical doctor in charge, the pharmaceutical manufacturer person in charge inputs a completed date of the survey form, and completes the survey form (operating procedure 31). By operating procedure 31 at the pharmaceutical manufacturer terminal 40, survey form managing system 100 remains the survey form status at the medical doctor side as "MANUFACTURE RECEIVED" and changes the survey form status at the pharmaceutical manufacturer side into "COMPLETED" (refer to FIG. 3).

The pharmaceutical manufacturer person in charge outputs a completed survey form from the pharmaceutical manufacturer terminal 40 (operating procedure 32).

Therefore, instead of electronically processing the survey form by the survey form managing system, the pharmaceutical manufacturer person in charge can visit the medical doctor in charge, and can manage the survey form (paper form) sealed by the medical doctor in charge.

FIG. 3 is a diagram showing an example of transition of the survey form status.

In FIG. 3, in the operating procedure 24 in accordance with FIG. 2, when the patient information is inputted at the medical doctor terminal 30, "NOT SEND" is set as a status of the medical doctor and "(blank)" is set as a status of the pharmaceutical manufacturer. In this status, the medical doctor is allowed to input, save, and refer to information on the survey form screen provided by the survey form managing system 100 at the medical doctor terminal 30. On the other hand, in this status, since the medical doctor in charge has not sent the survey form to the pharmaceutical manufacturer person in charge, it is impossible for the pharmaceutical manufacturer person in charge to refer to the survey form.

In the operating procedure 25, when the survey form has been sent by the medical doctor in charge, the status of the medical doctor is changed into "SENT" and "NEW ARRIVAL" is set as the status of the pharmaceutical manufacturer. In this status, it is possible for the medical doctor in charge only to refer to the survey form information but it is prohibited for the medical doctor in charge to input, update, and delete the information on the survey form. On the other hand, the pharmaceutical manufacturer person in charge is allowed only to refer to the information on the survey form and is allowed to input, save, refer to, and update the re-survey request information. In addition, in this status, when the pharmaceutical manufacturer person in charge decides that the input of the survey form is completed, it is possible for the pharmaceutical manufacturer person to input, save, and refer to the completed date on the survey form.

Furthermore, when a substitute medical doctor in charge cannot continue to input into the survey form or when the survey cannot be conducted for a long term because of a business trip or a like in a case in which the medical doctor cancels a survey, it becomes possible for the pharmaceutical manufacturer person in charge to input, save, and refer to a survey form collection not-available day and a collection not-available reason.

In the operating procedure 26, when the pharmaceutical manufacturer person in charge confirms survey form information at the pharmaceutical manufacturer terminal 40, the status of the medical doctor is changed into "MANUFACTURE RECEIVED", and the status of the pharmaceutical manufacturer is changed into "CONFIRMING". Similar to the operating procedure 25 in this status, the medical doctor in charge is allowed only to refer to the survey form information at the medical doctor terminal 30 but is prohibited from inputting, updating, and deleting the information on the survey form. On the other hand, similar to operating procedure 25, the pharmaceutical manufacturer person in charge is allowed only to refer to the survey form information and is allowed to input, save, refer to, and update the re-survey request information. Moreover, in this status, when the pharmaceutical manufacturer person in charge decides that the input of the survey form is completed, the pharmaceutical manufacturer person is allowed to input, save, and refer to the completed date on the survey form. Furthermore, when a substitute medical doctor in charge cannot continue to input into the survey form or when the survey cannot be conducted for a long term because of a business trip or a like in a case in which the medical doctor cancels survey, it becomes possible for the pharmaceutical manufacturer person in charge to input, save, and refer to the survey form collection not-available day and the collection not-available reason.

In the operating procedure 27, when the pharmaceutical manufacturer requests the re-survey at the pharmaceutical manufacturer terminal 40, the status of the medical doctor is changed into "NEW ARRIVAL", and the status of the pharmaceutical manufacturer is changed into "REQUESTING". In this status, the medical doctor in charge is allowed to refer to and update the survey form information and is allowed only to refer to re-survey request matters at the medical doctor terminal 30. On the other hand, the pharmaceutical manufacturer person in charge is allowed only to refer to the survey form information and the re-survey request information at the pharmaceutical manufacturer terminal 40. In addition, in this status, when a substitute medical doctor in charge cannot continue to input into the survey form or when the survey cannot be conducted for a long term because of a business trip or a like in a case in which the medical doctor cancels survey, it becomes possible for the pharmaceutical manufacturer person in charge to input, save, and refer to the survey form collection not-available day and the collection not-available reason.

In the operating procedure 28, when the medical doctor in charge at the medical doctor terminal 30 modifies the survey form information where the re-survey was requested, the status of the medical doctor is changed into "NOT SEND", and the status of the pharmaceutical manufacturer is not changed to remain as "REQUESTING". In this status, similar to the operation procedure 27, the medical doctor in charge is allowed to refer to and update the survey form information and is allowed to refer to the re-survey request matters at the medical doctor terminal 30. On the other hand, similar to the operation procedure 27, the pharmaceutical manufacturer person in charge is allowed only to refer to the survey form information and the re-survey request information at the pharmaceutical manufacturer terminal 40. In addition, in this status, when a substitute medical doctor in charge cannot continue to input into the survey form or when the survey cannot be conducted for a long term because of a business trip or a like in a case in which the medical doctor cancels survey, it becomes possible for the pharmaceutical manufacturer person in charge to input, save, and refer to the survey form collection not-available day and the collection not-available reason.

In the operating procedure 29, when the medical doctor sends survey form information at the medical doctor terminal 30, the status of the medical doctor is changed into "SENT" and the status of the pharmaceutical manufacturer is changed into "NEW ARRIVAL". In this status, similar to the operating procedure 28, the medical doctor in charge is allowed only to refer to the survey form information and the re-survey request information at the medical doctor terminal 30. On the other hand, the pharmaceutical manufacturer person in charge is allowed to refer to the survey form information and previous re-survey request information at the pharmaceutical manufacturer terminal 40. The pharmaceutical manufacturer person is also allowed to input, save; refer to, and update the re-survey request matters with respect to the survey form information currently received, at the pharmaceutical manufacturer terminal 40. Furthermore, in this status, when it is determined that the input of the survey form is completed, the pharmaceutical manufacturer person is allowed to input, save, and refer to the completed date on the survey form. Moreover, when a substitute medical doctor in charge cannot continue to input into the survey form or when the survey cannot be conducted for a long term because of a business trip or a like in a case in which the medical doctor cancels survey, it becomes possible for the pharmaceutical manufacturer person in charge to input, save, and refer to the survey form collection not-available day and the collection not-available reason.

In the operating procedure 30, when the pharmaceutical manufacturer person in charge confirms survey form information, the status of the medical doctor is changed into "MANUFACTURE RECEIVED", and the status of the pharmaceutical manufacturer is changed into "CONFIRMING". In this status, similar to the operating procedure 29, the medical doctor in charge is allowed only to refer to the survey form information and the re-survey request information at the medical doctor terminal 30. On the other hand, similar to the operating procedure 29, the pharmaceutical manufacturer person in charge is allowed to refer to the survey form information and the previous re-survey request information. Moreover, the pharmaceutical manufacturer person is allowed to input, save, refer to, and update the re-survey request matters with respect to the survey form information currently received.

In the operating procedure 31, when the pharmaceutical manufacturer person in charge inputs the completed date of the survey form into the survey form at the pharmaceutical manufacturer terminal 40, the status of the medical doctor is set as "MANUFACTURE RECEIVED", and the status of the pharmaceutical manufacturer is changed into "completion". In this status, both the medical doctor in charge and the pharmaceutical manufacturer person in charge are allowed only to refer to the survey form information.

The operating procedure 90 that is not shown in FIG. 2 shows a state transition when the survey form collection not-available day and the collection not-available reason are inputted at the pharmaceutical manufacturer terminal 40 between operating procedures 25 and 30. In this case, the status of the medical doctor status is changed into "MANUFACTURE RECEIVED", and the status of the pharmaceutical manufacturer is changed into "NOT-AVAILABLE". In this status, both the medical doctor in charge and the pharmaceutical manufacturer person in charge are allowed only to refer to the survey form information.

Since the above-mentioned status of the pharmaceutical manufacturer is displayed corresponding to the survey form in response to the operating procedure, the survey form can be easily managed in the same operating procedures even if the pharmaceutical manufacturer person in charge conducts the re-survey for many times with a plurality of the medical doctors, respectively, for the same or different protocol (denotes each survey).

Similarly, since the status of the above-mentioned medical doctor is displayed corresponding to the survey form in response to the operating procedure, in a case in which the medical doctor in charge surveys in accordance with the same or the different protocol with respect to institutions such as a plurality of hospitals where the medical doctor works, and in a case in which a plurality of the pharmaceutical manufacturer persons in charge conducts the survey, the survey form can be easily managed by the same operating procedures.

A hardware configuration of the survey form managing system corresponding to a data reliability verifying apparatus is shown in FIG. 4 according to the embodiment of the present invention.

In FIG. 4, this system includes a CPU (Central Processing Unit) 11, a memory unit 12, an output unit 13, an input unit 14, a display unit 15, an auxiliary storage unit 16, a CD-ROM drive unit 17, and a communication unit 18. Each of these units 11, 12, 13, 14, 15, 16, and 17 and the communication unit 18 are connected to a bus B.

The CPU 11 controls the survey form managing system in accordance with a program stored in the memory unit 12, and conducts a process in the survey form managing system that will be described later. The memory unit 12 includes a RAM (Random Access Memory) and a ROM (Read-Only Memory), and stores the program executed by the CPU 11, data required for the process conducted by the CPU 11, and data-obtained by the process conducted by the CPU 11, or a like. Moreover, areas of the memory unit 12 are partially assigned as a work area used for the process conducted by the CPU 11.

The output unit 13 includes a printer or a like and outputs a process result or specified information. The input unit 14 includes a mouse, a keyboard, or a like, and is used in order to input various information required for a manager of the survey form managing system to conduct the survey form managing process that will be described later. The display unit 15 displays various information required for the manager under a control of the CPU 11.

For example, the auxiliary storage unit 16 includes a hard disk unit, and stores various files and the program.

For example, the program according to the survey form managing process is provided by a CD-ROM 20 to the system. That is, when the CD-ROM 20 storing the program according to the survey form managing process is set to the CD-ROM drive unit 17, the CD-ROM drive unit 17 reads the program from the CD-ROM 20 and the program read from the CD-ROM 20 is installed into the auxiliary storage unit 16 through the bus B. And when this survey form managing process is activated, the CPU 11 starts the process in accordance with the program installed into the auxiliary storage unit 16. In addition, it is not limited to the CD-ROM 20 as a medium storing the program. Any computer-readable recording medium can be applied as the medium storing the program.

Next, a functional configuration of the survey form managing system for realizing processes corresponding to the above-mentioned operating procedures will be described with reference to FIG. 5.

Figure 5:
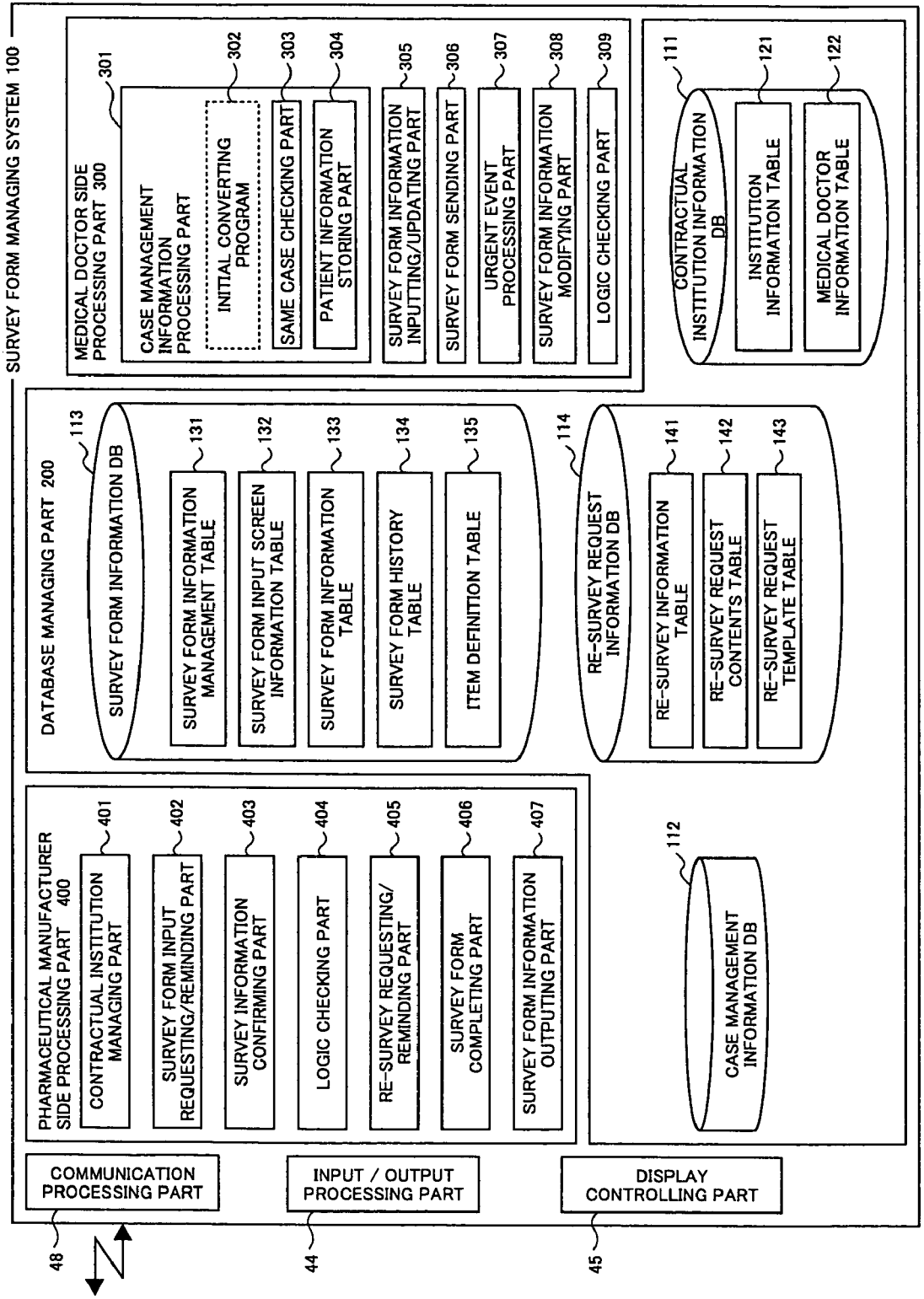
FIG. 5 is a diagram showing an example of a functional configuration of a survey form managing system.

FIG. 5 is a diagram showing an example of the functional configuration of the survey form managing system.

Referring to FIG. 5, the survey form managing system 100 mainly includes a database managing part 200 that stores and manages various databases to the auxiliary storage unit 16 in FIG. 4, a medical doctor side processing part 300 that executes the process in response to a process request in accordance with the above-mentioned operating procedures from the medical doctor terminal 30, a pharmaceutical manufacturer side processing part 400 that executes a process in response to a process request in accordance with the above-mentioned operating procedures from the pharmaceutical manufacturer terminal 40, a communications processing part 48 that conducts data communication through the Internet 50 by controlling the communication unit of FIG. 4, an input/output processing part 44 that controls a data input process from the input unit 14 of FIG. 4 and a data output process to the output unit 13 of FIG. 4, and a display controlling part 45 that controls a data display process to the display unit 15 of FIG. 4.

The database managing part 200 includes a contractual institution information DB 111 that manages information concerning the contractual institution and the medical doctor in charge inputted in the operating procedure 21 in FIG. 2, a case management information DB 112 that manages the case information inputted by the operating procedure 24, a survey form information DB 113 that manages the information concerning the survey form where information of the patient by whom the medicine was prescribed is inputted for each case in the operating procedure 25 based on the protocol, and a re-survey request information DB 114 that manages information concerning the re-survey request inputted in the operating procedure 27.

Furthermore, the contractual institution information DB 111 includes an institution information table 121 showing information of the hospital or the like where the medical doctor in charge works, and a medical doctor information table 122 showing information concerning the medical doctor in charge.

Moreover, the survey form information DB 113 includes a survey form information management table 131 that manages survey form management information for each case based on the protocol, a survey form input screen information table 132 that manages survey form input screen information showing a configuration of a survey form input screen, a survey form information table 133 that manages the survey form information inputted into the survey form, a survey form history table 134 that copies and manages the survey form information completed in the operating procedure 31, and an item definition table 135 that manages item definition for survey form input screen information to form a screen.

Moreover, the re-survey request information DB 114 includes a re-survey information table 141 that manages the re-survey information showing the re-survey request, and a re-survey request contents table 142 that manages re-survey request contents.

The medical doctor side processing part 300 includes a case management information processing part 301 including an initial converting program 302 that converts the patient name into initials in the operating procedure 24, a same case checking part 303 that confirms whether or not the same case has already been registered, and a patient information storing part 304 that stores and registers information of the patient, a survey form information inputting/updating part 305 that manages the survey form information inputted by the operating procedure 25, a survey form sending part 306 that sends the survey form completed by the operating procedure 25, an urgent event processing part 307 that sends e-mail when the information concerning the urgent event is in the survey form inputted by the operating procedure 25, and a survey form information modifying part 308 that manages the survey form modified in response to the re-survey request.

The case management information processing part 301 loads the initial converting program 302 into the medical doctor terminal 30, and activates the initial converting program 302 on the medical doctor terminal 30. That is, the patient name, which is inputted by the medical doctor in charge at the medical doctor terminal 30, is converted into the initials. Moreover, the case management information processing part 301 prevents duplicate registration of the same case by controlling the same case checking part 303. Furthermore, by controlling the patient information storing part 304, the case management information processing part 301 encrypts the patient name, and registers the patient information to the case management information DB 112.

Moreover, the same case checking part 303 searches the case management information DB 112 with a full name of the patient and a birth date of the patient, and confirms whether or not the same patient information is registered.

By controlling the survey form input screen information table 132 and the item definition table 135 of the survey form information DB 113, the survey form information inputting/updating part 305 forms a survey form screen, and provides the survey form screen to the doctor terminal 30 by the communication processing part 48. And the statuses of the medical doctor and the pharmaceutical manufacturer in the survey form management information table 131 are changed.

In the operating procedure 25, when it is completed to input to or update the survey form at the medical doctor terminal 30, the survey form sending part 306 updates the survey form information table 133. And the statuses of the medical doctor and the pharmaceutical manufacturer in the survey form management information table 131 are changed.

When the survey form information table 133 is updated by the survey form information inputting/updating part 305, the urgent event processing part 307 confirms whether or not the information concerning the serious urgent event for the survey form information is inputted. When the information concerning the urgent event is set, the urgent event processing part 307 sends the information to the pharmaceutical manufacturer person in charge by e-mail.

In the operating procedure 28, when the medical doctor in charge modifies the survey form at the medical doctor terminal 30 in response to the re-survey request, the survey form information modifying part 308 updates the survey form information table 133 of the survey form information DB 113. And the statuses of the medical doctor and the pharmaceutical manufacturer in the survey form management information table 131 are changed.

The pharmaceutical manufacturer side processing part 400 includes a contractual institution managing part 401, a survey form input requesting/reminding part 402, a survey information confirming part 403, a logic checking part 404, a re-survey requesting/reminding part 405, a survey form completing part 406, and a survey form information outputting part 407.

In the operating procedure 21, the contractual institution managing part 401 stores and manages the information concerning the contractual institution and the medical doctor in charge, which were registered from the pharmaceutical manufacturer terminal 40 in the institution information table 121 and the medical doctor information table 122 of the contractual institution information DB 111.

In the operating procedure 22, the pharmaceutical manufacturer person in charge requests the medical doctor in charge to input into the survey form, the survey form input requesting/reminding part 402 sends e-mail indicating a request to input a predetermined survey form to the medical doctor in charge. Moreover, in the operating procedure 23, when the pharmaceutical manufacturer person in charge reminds the medical doctor in charge to input into the survey form, the survey form input requesting/reminding part 402 sends e-mail showing a reminder to input into the survey form to the medical doctor in charge.

When the pharmaceutical manufacturer person in charge selects the survey form at the pharmaceutical manufacturer terminal 40 in the operating procedure 26 or the operating procedure 30, the survey information confirming part 403 retrieves the survey form selected by the pharmaceutical manufacturer person in charge from the survey form information table 133 of the survey form information DB 113, and activates the logic checking part 404. The survey information confirming part 403 provides the retrieved survey form and the execution result of the logic check executed by the logic checking part 404 to the pharmaceutical manufacturer terminal 40. Moreover, the statuses of the medical doctor and the pharmaceutical manufacturer of the survey form management information table 131 are changed.

The logic checking part 404 executes the logic check for the item with a mark that specifies the logic check managed on the item definition table 135. For example, a single item check is executed. The single item check confirms whether or not an information item showing the date of the survey form retrieved by the survey information confirming part 403 and information items mandatory to input are properly input. And the single item check confirms whether or not each information item inputted by the medical doctor is within a proper data range. Moreover, the logic checking part 404 executes the logic check checking whether or not it is logically acceptable between the information items.

In the operating procedure 27, when the pharmaceutical manufacturer person in charge conducts the re-survey request to the medical doctor in charge, the re-survey requesting/reminding part 405 sends the e-mail showing the predetermined re-survey request from the pharmaceutical manufacturer person in charge to the medical doctor in charge, and changes the statuses of the medical doctor and the pharmaceutical manufacturer of the survey form management information table 131. Moreover, when the pharmaceutical manufacturer person in charge reminds the medical doctor in charge to re-survey, the re-survey requesting/reminding part 405 sends e-mail showing a reminder to conduct the predetermined re-survey to the medical doctor in charge.

In the operating procedure 31, when the survey form completed date is inputted by the pharmaceutical manufacturer person in charge at the pharmaceutical manufacturer terminal 40, the survey form completing part 406 retrieves the survey form into which the survey form completed date was inputted from the survey form information table 133 of the survey form information DB 113, and copies the survey form into the survey form history information table 134. Furthermore, the survey form completing part 406 stores the completed survey form as image data. The completed survey form becomes impossible to be modified after that.

For example, the image data are stored in a PDF (Portable Document File) form.

Accordingly, since an authentication confirmation is conducted based on the authentication information of the medical doctor in charge appended to the survey form, it is possible to guarantee reliability of the information on the survey form even if the survey form managing system 100 is installed in the pharmaceutical manufacturer side.

In the operating procedure 32, when the survey form completed by the pharmaceutical manufacturer person in charge is output, the survey form information outputting part 407 retrieves the survey form, which is to be output, from the survey form information table 133 of the survey form information DB 113, and downloads the survey form to the pharmaceutical manufacturer terminal 40.

The logic checking part 309, which includes a function equivalent to the logic checking part 404 of the pharmaceutical manufacturer side processing part 400, is provided in the medical doctor side processing part 300, and the function may be suitably activated from the survey form information inputting/updating part 305 and the survey form information modifying part 308.

Next, an initial converting process by the initial converting program 302 will be described with reference to FIG. 6.

Figure 6:
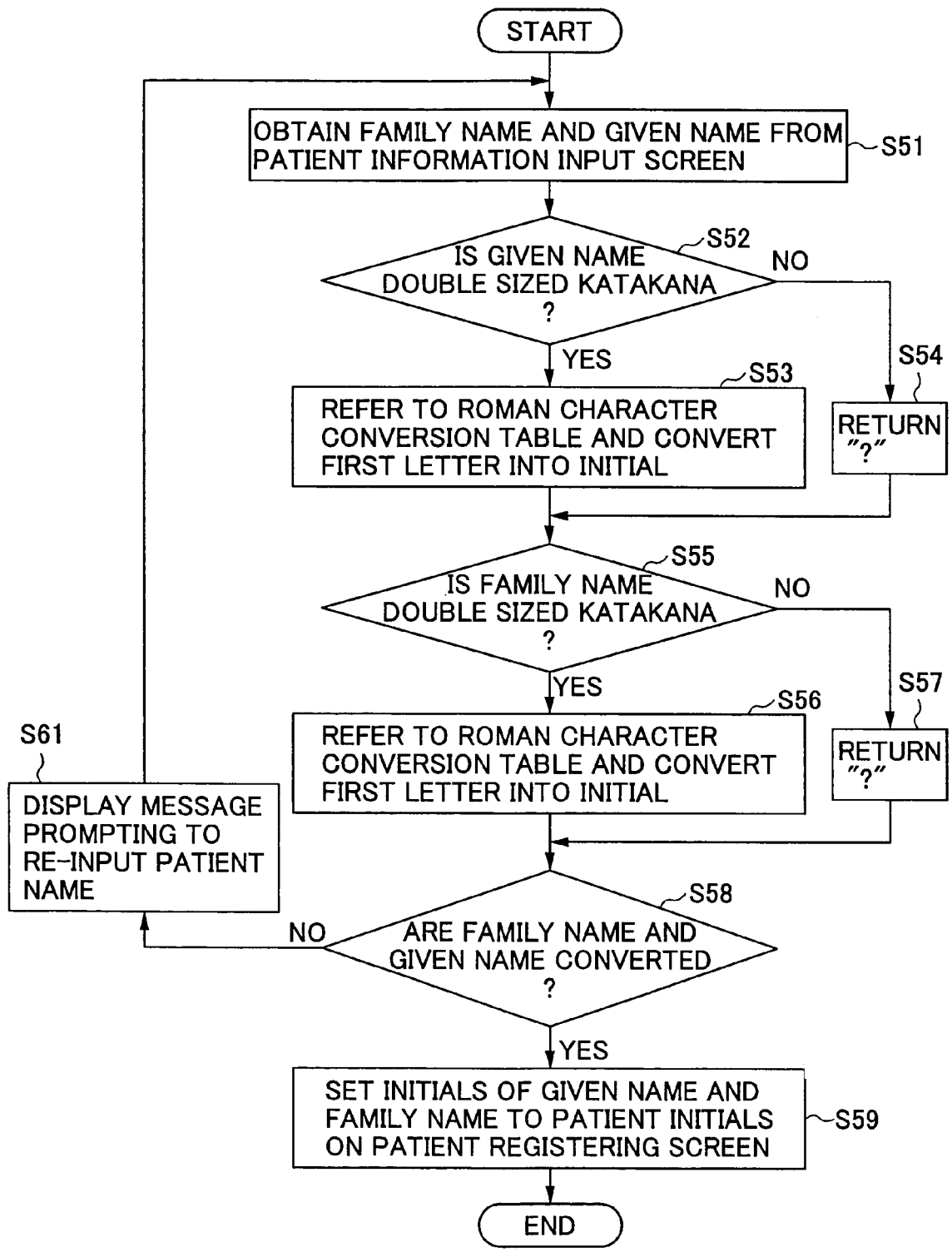
FIG. 6 is a flowchart diagram explaining an initial converting process.

FIG. 6 is a flowchart diagram explaining the initial converting process.

Referring to FIG. 6, the family name and given name inputted by the medical doctor in charge are obtained from the patient information input screen (step S51).

It is determined whether or not an obtained given name is a double sized katakana character (step S52). When the given name is not the double sized katakana character, "?" is returned (step S54) and the process goes to a step S55. When the given name is the double sized katakana character, a first character is converted into an initial with reference to a Roman character conversion table (step S53).

The Roman character conversion table may be just a table corresponding the alphabet to each katakana character.

Subsequently, it is determined whether or not an obtained family name is the double sized katakana character (step S55). When the family name is not a double sized katakana character, "?" is returned (step S57) and the process goes to a step S58. When the family name is the double sized katakana character, a first character is converted into an initial with reference to the Roman character conversion table (step S56).

It is determined whether or not the family name and the given name are converted into the initials (step S58). When the family name and the given name are not converted into the initials, a message prompting re-input of the patient name is displayed (step S61), and the process goes back to the step S51. When the family name and the given name are converted into the initials, the initials are linked and displayed in an initial display area on a patient registration screen (step S59). Then, the initial converting process is terminated.

A process by the same case checking part 303 of the medical doctor side processing part 300 is described with reference to FIG. 7.

Figure 7:
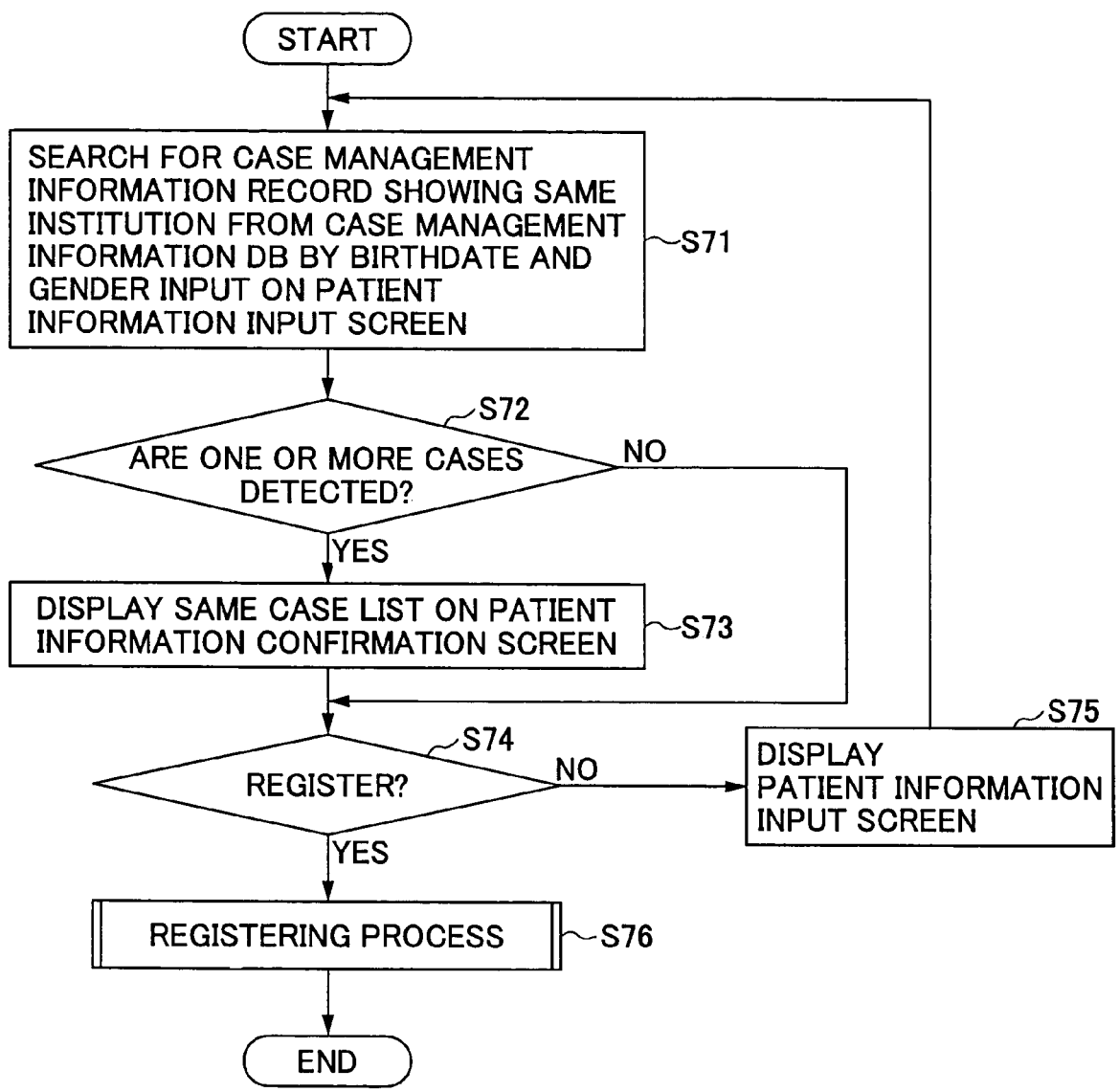
FIG. 7 is a flowchart diagram explaining a same case check process.

FIG. 7 is a flowchart diagram explaining a same case check process.

Referring to FIG. 7, based on the birth date and gender of the patient that are inputted into the patient information input screen by the medical doctor in charge, the case management information record showing the same institution is searched from the case management information DB 112 (step S71).

It is determined whether or not the one or more same cases are detected (step S72). When there is no case detected, the process goes to a step S74. When one or more cases are detected, a list of the same cases is displayed on a patient information confirmation screen (step S73).

It is determined whether or not the patient information input on the patient information input screen is registered (step S74). For example, it is determined whether or not a "next" or "register" button is clicked by the medical doctor in charge. When the "register" button is not clicked, the patient information input screen is displayed again (step S75) so as to prompt the medical doctor to modify patient information, and the process goes back to step S71. When the "register" button is clicked, a registering process is executed (step S76) and the same case checking process is terminated. The registering process is executed by the patient information storing part 304 of the medical doctor side processing part 300 of FIG. 5.

In the following, details of a survey form management method will be described, referring to the display screen.

FIG. 8 is a diagram showing an example of a survey form management screen provided to the pharmaceutical manufacturer terminal.

Referring to FIG. 8, a survey form management screen 500 provided to the pharmaceutical manufacturer terminal 40 includes a search condition input area 5001 for searching for a desired survey form, a contractual institution information input area 5002 for inputting and editing the contractual institution information, and a survey form list display area 5003 that displays a survey form list based on a user ID of the pharmaceutical manufacturer person in charge.

A search condition input area 5001 includes a search condition 502 that selects and searches for a protocol, a search condition 503 that searches for the institution where the survey form input request is not conducted with respect to the medical doctor in charge, a search condition 504 that searches by a date, a search condition 505 that searches by information concerning an MR (Medical Representative) in charge, a search condition 506 that searches by information concerning the medical doctor in charge, and a search button 507 for executing a search.

The pharmaceutical manufacturer person in charge inputs one or more of the search conditions 502 through 506, and clicks the search button 507. Consequently, the survey form list as a search result is displayed at the survey form list display area 5003.

The contractual institution information input area 5002 includes a new contractual institution input button 510 for inputting information of a new contractual institution and a new medical doctor, a contractual institution information update button 511 for updating the information of the contractual institution and the medical doctor, an input request/reminder button 512 for sending an input request or reminder of the survey form to the medical doctor in charge, and a medical doctor change button 513 for changing the medical doctor in charge for the survey form into which input is completed.

The pharmaceutical manufacturer person in charge clicks any one of the buttons 510 through 513 and a corresponding screen (mentioned later) is displayed.

The survey form list display area 5003 displays the survey form list based on the user ID inputted by the pharmaceutical manufacturer person in charge when the pharmaceutical manufacturer person in charge accessed the survey form managing system. For example, the survey form list that is displayed at the survey form list display area 5003 includes items: "CHECK BOX" for selecting the survey form as shown in a list table 514, "REQUESTED DATE" and "REMINDED DATE" showing dates requested and reminded to input into the survey form, "INSTITUTION NAME" and "SURVEY REQUEST INSTITUTION NO.", "MR IN CHARGE" as a business signature and a collection person, "CONTRACTED DATE" when a contract concerning a medicine survey is concluded, "CONTRACT TERM" that shows a start day and an expiration day of the contract, "CONTRACT CASE" showing the number of cases that are contracted, "MEDICAL DOCTOR NAME (SECTION NAME)" showing the medical doctor who conducts the survey, "SURVEY FORM STATUS" showing progress with respect to the number of contract cases, and a like. Moreover, for example, the survey form status includes status items of "OBTAINED", "NEW ARRIVAL", "CONFIRMING", "REQUESTING", "COMPLETION AND NOT AVAILABLE", and a like, according to the status of the pharmaceutical manufacturer of FIG. 3 for each medical doctor in charge. The survey form status displays the number of cases corresponding to each status item.

The pharmaceutical manufacturer person in charge clicks the check box of the list table 514, and clicks the input request/reminder button 512. Then, the pharmaceutical manufacturer person conducts an input request or reminder to the medical doctor in charge.

When the pharmaceutical manufacturer person in charge clicks the new contractual institution input button 510, a contractual institution input screen 520 as shown in FIG. 9 is displayed.

FIG. 9 is a diagram showing an example of the contractual institution input screen for the pharmaceutical manufacturer to input contractual institution information.

Referring to FIG. 9, a contractual institution input screen 520 includes an operation button area 5201 that operates to store input information, an institution information input area 5202 that inputs information concerning the new contractual institution, a medical doctor information input area 5203 that inputs information concerning the medical doctor in charge, and a like.

The institution information input area 5202 includes items of "SURVEY REQUEST INSTITUTION NUMBER" numbered to each survey request, "CONTRACTED DATE" when a contract concerning the survey of a medicine is concluded, "CONTRACT TERM" that shows a start day and an expiration day of the contract, "CONTRACT CASE", "INSTITUTION NAME" that shows a hospital name, "INSTITUTION CODE" for specifying an institution, "BRANCH NAME" which an MR in charge of a branch as a collector belongs to, "BRANCH CODE" for specifying a place of business, "MR IN CHARGE" showing a name of the MR, "EMPLOYEE CODE" of the MR in charge, "E-MAIL" showing an e-mail address of the MR in charge, and a like.

The medical doctor information input area 5203 includes items of "DELETE" that is selected to delete medical doctor information that is saved, "USER ID" that specifies the medical doctor, "NAME" of the medical doctor, "SECTION NAME" of the medical doctor, "SECTION CODE" that specifies the section name, and a like. In the "DELETE" item, "NEW" is displayed when there is no medical doctor information that is stored, and a check box is displayed when there is the medical doctor information that is stored. When there is the medical doctor information that is stored and to be deleted, the check box is clicked to select the medical doctor information, and a delete button 522 is clicked. By this operation, the medical doctor information after stored is deleted.

For example, the pharmaceutical manufacturer person in charge inputs "20000101" to the contracted date, "20001010-20011010" to the contract term, "150" to the contract case, "ABC HOSPITAL" to the institution name, "EAST JAPAN BRANCH" to the branch name, "FUJIMI, ICHIRO" to the MR in charge, "001" to the employee code, and "tro@sei.fip" to the e-mail in the institution information input area 5202. And the pharmaceutical manufacturer person inputs "DOC1" to the user ID, "IYAMA, SHIRO" to the name, "PHYSICIAN" to the section name, and "002" to the section code, and clicks a save button 521 in the medical doctor information input area 5203 (operation procedure 21). By this operation, the contractual institution managing part 401 of the pharmaceutical manufacturer side processing part 400 of FIG. 5 is activated. And the input information of the institution information input area 5202 is stored in the institution information table 121 of the contractual institution information DB 111, and the input information of the medical doctor information input area 5203 is stored in the medical doctor information table 122.

When the input information of the medical doctor information input area 5203 is stored, a message "SAVING PROCESS IS NORMALLY COMPLETED" is displayed at a message display area 525.

When the back button 523 is clicked to go back to the survey form management screen 500, the list table 514 is updated by the input information saved in the contractual institution input screen 520.

Figure 10:
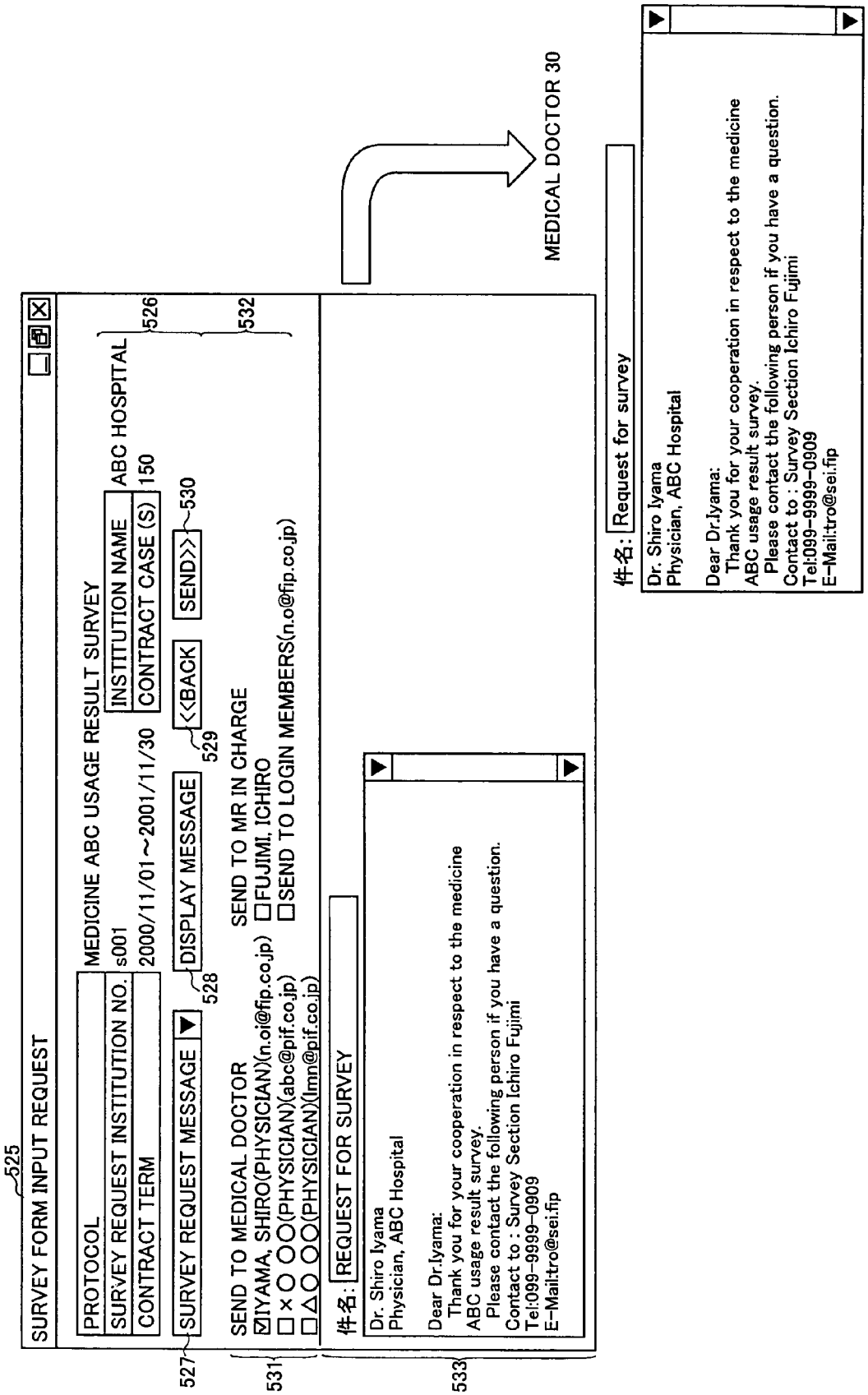
FIG. 10 is a diagram showing an example of an e-mail of a survey form input request.

At the survey form management screen 500 of FIG. 8, for example, when in order to select the "ABC hospital" from the list table 514, a pharmaceutical manufacturer person in charge clicks a check box 515 and clicks the request/reminder button 512 (the operating procedures 22 or 23), the survey form input request screen as shown in FIG. 10 is displayed.

FIG. 10 is a diagram showing an example of e-mail of the survey form input request.

Referring to FIG. 10, the survey form input request screen 525 includes a selection information-display area 526 that displays the institution information selected by the pharmaceutical manufacturer person in charge, a selection area 527 that selects a predetermined e-mail message, a message display button 528 for displaying the selected the e-mail message, a back button 529 for going back to a previous screen (survey form management screen), a send button 530 for sending an e-mail, a medical doctor selection area 531 for selecting a medical doctor, a selection area 532 for selecting the transmission place of the same e-mail, and an e-mail area 533 that displays the e-mail message.

For example, when the pharmaceutical manufacturer person in charge selects a "survey request message" from the selection area 527, selects the medical doctor "SHIRO IYAMA" in charge from the medical doctor selection area 531, and clicks the message display button 528, the e-mail message in which the medical doctor name in charge is set is displayed based in the e-mail area 533 on a predetermined "survey request message".

When the pharmaceuticals manufacture person in charge confirms the displayed e-mail message and clicks the send button 530, this e-mail message is sent to the medical doctor (for example, Dr, Shiro Iyama) in charge.

When the e-mail of the survey form input request is sent to the medical doctor in charge, "2000/01/01" is displayed at an upper row of the item of requested date and reminded date of the institution name "ABC hospital" of the list table 514 in the survey form management screen 500 shown in FIG. 8. Similarly, when the pharmaceutical manufacturer person in charge sends the e-mail of reminder of the predetermined survey request is shown to the medical doctor "SHIRO IYAMA" in charge, "2000/01/02" is displayed on the lower row of the item of the requested date and the reminded date.

Next, the survey form management method at the medical doctor terminal 30 is described in that the medical doctor in charge received the e-mail showing the survey form input request.

FIG. 11 is a diagram showing an example of the protocol selection screen to which a medical doctor terminal is provided.

The protocol selection screen 600 is displayed based on a user ID that is inputted by the medical doctor in charge when the medical doctor connects to the survey form managing system 100.

A protocol list table 601 includes items of "INSTITUTION NAME" and "SECTION NAME", "CONTRACT TERM" that shows survey start date and end date of a medicine based on a contract, "CONTRACT CASE", "INPUT CASE" that shows the number of current input cases, "NEW ARRIVAL" showing the number of the survey forms as the new arrivals of the request from the pharmaceutical manufacturer person in charge, "NOT SENT" that shows the number of the survey forms that have not been sent, "SENT" that shows the number of the survey forms that have already been sent, "NEW REGISTRATION" for registering a new case, and a like. The items of the "INPUT CASE", the "NEW ARRIVAL", the "NOT SENT", and the "SENT" are shown as a numeral with an underline. When the medical doctor in charge clicks the numeral of the item that the medical doctor wants to refer to, a list concerning that item is displayed. When the "INPUT CASE" item is clicked, a list of cases currently inputted is displayed. When the "NEW ARRIVAL" item is clicked, a list of cases including newly arrived survey forms is displayed. When the "NOT SEND" item is clicked, a list of cases including the survey form in a state of the "NOT SENT" is displayed. When the "SENT" item is clicked, a list of cases in which all survey forms are sent or received by the pharmaceutical manufacturer is displayed.

In a case in which the medical doctor in charge who works for four institutions surveys the medicine from three pharmaceutical manufacturers, for example, as shown in the protocol list table 601, the protocol information is displayed for each institution with respect to protocol information 602 concerning the protocol name "MEDICINE ABC" and the manufacture "PHARMACEUTICAL MANUFACTURER 1", protocol information 603 concerning the protocol name "MEDICINE LMN" and the manufacture "PHARMACEUTICAL MANUFACTURER 6", protocol information 604 concerning the protocol name "MEDICINE XYZ" and the manufacture "PHARMACEUTICAL MANUFACTURER 8".

Therefore, from the protocol information 602 of the protocol list table 601, it is shown that the medicine ABC is surveyed in the institutions "ABC HOSPITAL", "TOKYO HOSPITAL", "YAMANOTE HOSPITAL", and "OO GENERAL HOSPITAL". From the protocol information 603, it is shown that the medicine LMN is surveyed in the institutions "ABC HOSPITAL", "YAMANOTE HOSPITAL", and "OO GENERAL HOSPITAL". From the protocol information 604, it is shown that the medicine XYZ is surveyed in the institutions "TOKYO HOSPITAL" and "OO GENERAL HOSPITAL".

Since the medical doctor in charge can easily confirm a progress of the survey request from each pharmaceutical manufacturer on one screen, the medical doctor is not required to manage the survey requests for each pharmaceutical manufacturer.

Screens for inputting the patient information will be described with reference to FIG. 12A through FIG. 12C.

For example, in a protocol selection screen 600 of FIG. 11, when the patient information is inputted into a new survey request at the institution "ABC HOSPITAL" where the protocol name "MEDICINE ABC" is surveyed, the medical doctor in charge clicks a new button 605.

By clicking the new button 605 by the medical doctor in charge, the patient information input screen as shown in FIG. 12A is displayed. In the patient information input screen, the medical doctor in charge inputs the patient information (case information) (the operating procedure 24).

Referring to FIG. 12A, the patient information input screen 610 includes a display area 611 that displays the protocol information selected by the medical doctor in charge, a patient information input area 612 for inputting patient information, a next button 613 for going to a next screen, and a back button 614 for going back to a previous screen.

The patient information input area 612 includes an input area for inputting a patient name, gender, a birth date, and a like, and an initials display area that is displayed by clicking an initial conversion 6120.

The medical doctor in charge inputs a family name and a given name separately in katakana for the patient name, referring to a chart. For example, the "FUJI" is inputted as the family name and the "TARO" is inputted as the given name. Then, the initial conversion 6120 is clicked. By clicking the initial conversion 6120, the initial converting program 302 loaded into the medical doctor terminal 30 is activated, and the initials "TF" are displayed on the initial display area of the patient information input area 612 of the patient information input screen 610. Subsequently, the medical doctor in charge inputs the gender, the birth date, and the chart number. After inputting into the patient information input area 612, the next button 613 is clicked to confirm the input patient information.

When the medical doctor in charge clicks the button 613, the same case checking part 303 of the medical doctor side processing part 300 of FIG. 5 starts, and also, a patient information confirmation screen 615 as shown in FIG. 12B is displayed.

Referring to FIG. 12B, the patient information confirmation screen 615 includes a display area 616 that displays the protocol information selected by the medical doctor in charge, a display area 617 that shows the patient information inputted into the patient information input area 612 by the medical doctor in charge, a message indicator area 619 that displays the message which prompts the medical doctor in charge to confirm the patient information, a same case display area 620 that shows the same case list as the execution result of a same case checking part 303, a next button 621 for going to a next screen, and a back button 622 for going back to a previous screen.

The display area 617 displays information inputted at the patient information input area 612 of the patient information input screen 610, and also, displays a portrait 618 corresponding to a patient age and gender. The case management information processing part 301 of the medical doctor side processing part 300 of FIG. 5 calculates the patient age based on the patient birth date as of a registered date. For example, based on a portrait table 625 as shown in FIG. 12C, the portrait corresponding to age and gender is displayed.

By displaying the portrait 618, when the medical doctor in charge confirms the input information on the patient information confirmation screen 615, the medical doctor in charge can determine whether or not the patient information inputted by the medical doctor are visually properly.

When the medical doctor in charge clicks the next button 621, the patient information storage part 304 of the medical doctor side processing part 300 of FIG. 5 stores the patient information inputted by the medical doctor as case information into the case management information DB 112.

On the other hand, when the medical doctor in charge clicks the back button 622, the patient information inputted by the medical doctor is deleted. Therefore, the duplicate registration of the same patient information can be prevented.

Next, in the operating procedure 25 of FIG. 2, The survey form information input screen for the medical doctor in charge to input the information to the survey form will be described.

FIG. 13 is a diagram showing a first example of the survey form information input screen.

Referring to FIG. 13, a survey form information input screen 630 as the first example includes a display area 641 that displays the information concerning the protocol selected by the medical doctor at the protocol selection screen 600 of FIG. 11, and a survey form input area 640 for inputting the information into the survey form.

The display area 641 includes a display area 631 including a protocol name and an institution name, a display area 632 that displays case information, a display area 633 that displays a survey form name and the survey form status, a page selection area 634 for selecting the page of the survey form displayed in the survey form input area 640, a back button 636 for going back to a previous screen, and a help button 637 for displaying an explanation of an input method for the survey form information input screen 630.

The display area 632 displays a case number, initials of a patient name, gender, a birth date, and a chart number.

The display area 633 displays a survey form name, and a state according to a survey form status of the medical doctor shown in FIG. 3.

The page selection area 634 includes a selection input area for selecting a page, and a screen switch button 635 for displaying the selected page.

For example, when the medical doctor in charge selects "PATIENT BACKGROUND" from the page selection area 634 and clicks the screen switch button 635, the survey form information inputting/updating part 305 of the medical doctor side processing part 300 of FIG. 5 is activated. The survey form information inputting/updating part 305 refers to the survey form input screen information table 132 and the item definition table 135 of the survey form information DB 113 based on the selected page "PATIENT BACKGROUND", and then, forms the "PATIENT BACKGROUND" page and displays the "PATIENT BACKGROUND" page on the survey form input area 640.

For example, the page "PATIENT BACKGROUND" includes input areas for items of "PATIENT INITIALS", "GENDER", "PREGNANCY INFORMATION", "BIRTH DATE", "CHART NO.", "MEDICAL EXAMINATION STATE" under administration, "WEIGHT" at a start of administration, "REASON FOR USE", "DISEASE FACTOR" (basic factor), "SERIOUSNESS DEGREE", "COMPLICATION", "IDIOSYNCRASIA", and "ANAMNESIS", and a save button 643, and a like.

Figure 14:
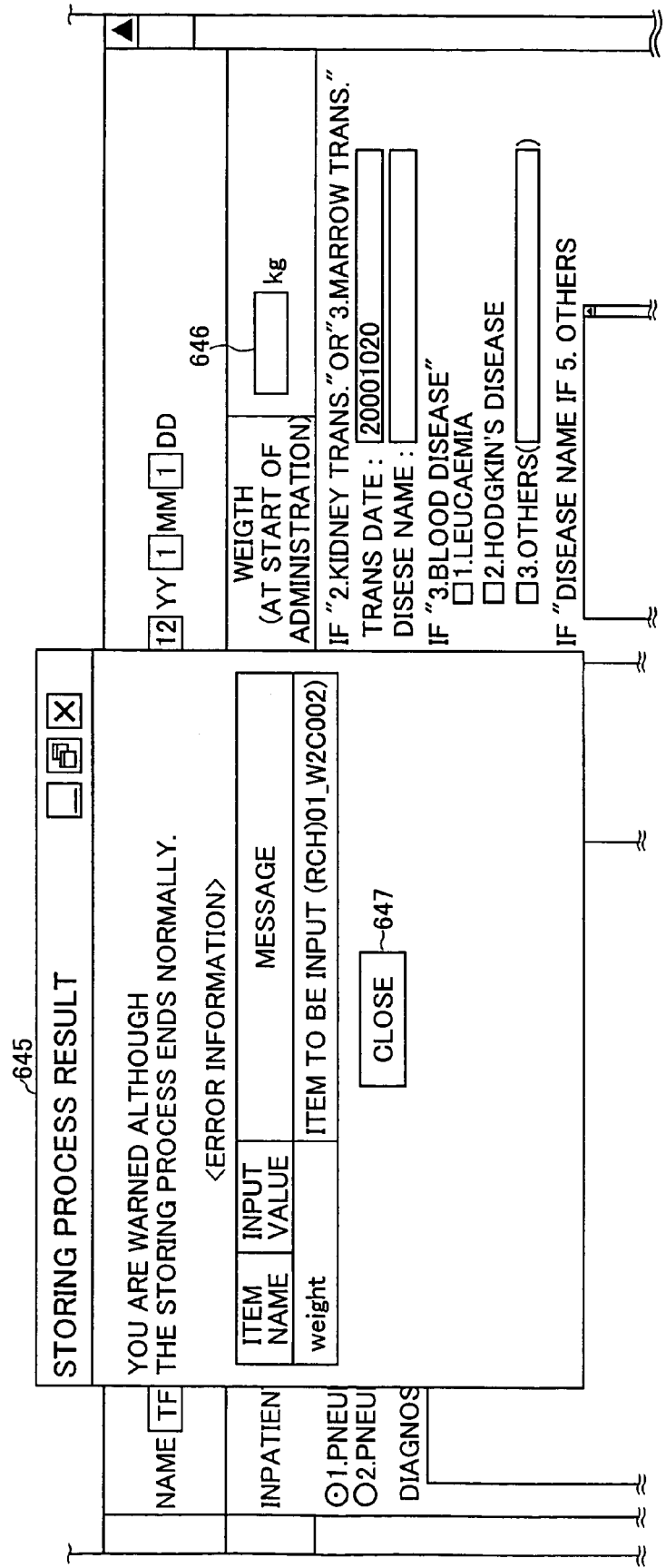
FIG. 14 is a diagram showing an example of a storage process result screen.

When the medical doctor in charge clicks the save button 643 after inputting information to the displayed page "PATIENT BACKGROUND", the logic checking part 309 of the medical doctor side processing part 300 of FIG. 5 is activated, and determines whether or not there is an error for the logic check in the information inputted by the medical doctor in charge, and displays a check result at a storing process result screen 645 as shown in FIG. 14.

The medical doctor in charge can know by the check result shown at the storing process result screen 645 that an input area 646 for a weight is not inputted. The medical doctor in charge clicks a close button 647 of the storing process result screen 645, closes the storing process result screen 645, and inputs weight into the input area 646. When the medical doctor in charge clicks the save button 643 of the survey form input area 640 again and an error is not detected by the logic check, the medical doctor similarly conducts to input information to another page.

Other examples of the page selection will be described with reference to FIG. 15A and FIG. 15B.

Referring to FIG. 15A, the survey form to which the medical doctor in charge inputs information is formed by pages of a patient background, a medical treatment progress, a clinical progress, a clinical laboratory value, adverse events 1, adverse events 2, adverse events 3, and a comment about adverse events.

When the medical doctor in charge selects the "MEDICAL TREATMENT PROGRESS" from the page list displayed by the page selection 634 and clicks the screen switch button 635, input items for the "MEDICAL TREATMENT PROGRESS" are displayed on the survey form input area 640 of the survey form information input screen 630 as a second example, as shown in FIG. 15B.

When the medical doctor in charge selects the "ADVERSE EVENTS 2", input items for the "ADVERSE EVENTS 2" are displayed on the survey form input area 640 of the survey form information input screen 630 as a third example, as shown in FIG. 16A.

When the medical doctor in charge selects the "ABOUT ADVERSE EVENTS", the area capable of inputting the "ABOUT ADVERSE EVENTS", such as an adverse drug reaction and a like, into the survey form input area 640 is displayed as shown in FIG. 16B.

Whenever the medical doctor in charge stores each page of the survey form, the survey form information inputting/updating part 305 of the medical doctor side processing part 300 of FIG. 5 stores the input information in the survey form information table 133 of the survey form information DB 113.

A screen for sending the survey form will be described with reference to FIG. 17A and FIG. 17B.

When the medical doctor in charge inputs all pages of the survey form, the medical doctor in charge clicks a numeral with the underline of the "NOT SENT" item corresponding to the protocol which is to send to the pharmaceutical manufacturer person in charge, from the protocol list table 601 of the protocol selection screen 600 shown in FIG. 11.

A patient selection screen 650 as shown in FIG. 17A is displayed by a click of the medical doctor in charge.

Referring to FIG. 17A, the patient selection screen 650 includes a display area 651 that displays protocol information selected by the medical doctor in charge, a case list 652 that displays a case list, and a back button 653 for going back to a previous screen.

In accordance with transition of the survey form status of FIG. 3, the case list 652 includes items of "STATUS" that displays the survey form status for each case, "PATIENT NAME" and "GENDER", "BIRTH DATE" and "CASE REGISTRATION NO.", "CHART NO.", "ADMINISTRATION START DATE" and "ADMINISTRATION END DATE", and "PATIENT BACKGROUND CHANGE".

When the "STATUS" item shows "NEW ARRIVAL", it shows that the re-survey has been requested by the pharmaceutical manufacturer person in charge (the operation procedure 27). Moreover, when the "NOT SENT" is shown, it shows that the survey form is being modified by the medical doctor in charge (the operation procedure 28).

For example, when the medical doctor in charge sends the survey form of a patient name "FUJI, TARO", the medical doctor clicks "NOT SENT" 654.

By this click of the medical doctor, a survey form selection screen 655 as shown in FIG. 17B is displayed.

Referring to FIG. 17B, the survey form selection screen 655 includes a display area 656 that displays the protocol information selected by the medical doctor in charge, patient information 657 that shows case information (patient information), operation items 658 that display operation items to the selected survey form, and a back button 660 for going back to a previous screen.

The medical doctor in charge confirms contents of the displayed patient information 657. When the medical doctor wants to send the survey form, the medical doctor clicks a send item value from the operation items 658. When the medical doctor wants to delete, the medical doctor clicks a delete item value.

When the medical doctor in charge clicks the send item value 659, a confirmation screen 661 is displayed. When sending the survey form, the medical doctor in charge clicks the OK button 662. And when canceling to send the survey form, the medical doctor clicks the cancel button 663.

When the medical doctor in charge clicks the OK button 662 of the confirmation screen 661, the survey form sending part 306 and the urgent event processing part 307 of the medical doctor side processing part 300 of FIG. 5 are activated. The survey form sending part 306 changes the survey form status of the survey form that is stored in the survey form management information table 131 of the survey-form information DB 113 and is sent by the medical doctor.

The urgent event processing part 307 determines whether or not there is an item where the adverse event flag is set to ON beforehand and where the medical doctor in charge inputs information, in pages or page items of the selected survey form. For example, in a case in which information is inputted to a pregnancy item 644 of the "PATIENT BACKGROUND" page displayed on the survey form input area 640 of FIG. 13, or pages of the "ADVERSE EVENTS 1", the "ADVERSE EVENTS 2", the "ADVERSE EVENTS 3", the "COMMENT ABOUT ADVERSE EVENTS" and a like of the page list shown in FIG. 15 (A), the urgent event processing part 307 sends e-mail showing that the urgent event occurred to the pharmaceutical manufacturer (the operating procedure 25).

For example, the e-mail showing that the urgent event occurred and is sent to the pharmaceutical manufacturer includes contents as shown in FIG. 18.

Referring to FIG. 18, e-mail 669 showing that the urgent event occurred includes a receiver 665, a message 666 informing that the urgent event occurred, an institution name 667 of the institution that is surveyed, a case list 668 that shows cases by a list.

For example, the case list 668 shows a case registration number, patient initials, a birth date, gender, and a type for each case.

By informing the pharmaceutical manufacturer by such e-mail 669, the pharmaceutical manufacturer person in charge can know immediately that the urgent event occurred. Also, the pharmaceutical manufacturer person can refer to the survey form of the patient showing that the urgent event occurred. Consequently, it is possible for the pharmaceutical manufacturer person to speedily manage the urgent event for the patient and make a prompt report to the Ministry of Health and Welfare.

Next, in the operating procedure 26, confirmation and the logic check of the survey form information by the pharmaceutical manufacturer person in charge will be described.

Referring to the survey form management screen 500 of FIG. 8, for example, when the pharmaceutical manufacturer person in charge clicks the new arrival 516 of the medical doctor "IYAMA, SHIRO", the survey form information confirming part 403 of the pharmaceutical manufacturer side processing part 400 of FIG. 5 is activated. Then, the survey form selection screen 700 as shown in FIG. 19A is displayed.

Referring to FIG. 19A, the survey form selection screen 700 includes a display area 671 that displays the information on the protocol selected by the pharmaceutical manufacturer person in charge, a re-survey request button 672 for requesting a re-survey, a re-survey reminder button 673 for prompting after the request of a re-survey, a back button 674 for going back to a previous screen, and a survey form list 675 that shows the survey forms.

The survey form list 675 includes, for each survey form, items of "STATUS" that shows the survey form status, "SURVEY FORM", "LOGIC CHECK", "INITIALS" and "GENDER" of a patient, "BIRTH DATE" and "CASE REGISTRATION NO.", "SURVEY FORM NAME", "SURVEY FORM COMPLETED DATE" showing a date when the survey form is completed, and a like.

The pharmaceutical manufacturer person in charge clicks the logic check button 678 to execute the logic check of the survey form where the status shows the "NEW ARRIVAL".

When the pharmaceutical manufacturer person in charge clicks the logic check button 678, the logic checking part 404 of the pharmaceutical manufacturer side processing part 400 of FIG. 5 is activated. The logic check result by the logic checking part 404 is informed to the pharmaceutical manufacturer person in charge by a logic check result screen 710 as shown in FIG. 19B.

The pharmaceutical manufacturer person in charge clicks a back button 711 of the logic check result screen 710, and clicks the survey form item of the survey form list 675 of the survey form selection screen 700 of FIG. 19A.

FIG. 20 is a diagram showing an example of the survey form information screen.

Referring to FIG. 20, the survey form information screen 730 includes a display area 741 that displays the information concerning the survey form selected by the pharmaceutical manufacturer person in charge, and a survey form display area 740 for inputting the information into the survey form.

The display area 741 includes a display area 731 including a protocol name and an institution name, a display area 732 that displays case information, a display area 733 that displays a survey form name and a survey form status, a page selection area 734 that selects a page of the survey form displayed in the survey form display area 740, a back button 736 for going back to a previous screen, and a help button 737 for displaying an explanation of the input method to the survey form input screen.

The display area 732 displays "CASE NO." and "INITIALS" of a patient name, "GENDER", "BIRTH DATE", "CHART NO.", and a like.

The display area 733 displays "SURVEY FORM NAME", and a status displayed according to the survey form status of the medical doctor shown in FIG. 3.

The page selection area 734 includes a selection input area for selecting a page, and a screen switch button 735 for displaying the selected page.

For example, when the pharmaceutical manufacturer person in charge selects "PATIENT BACKGROUND" from the page selection area 734, and clicks the screen switch button 735, the "PATIENT BACKGROUND" page is displayed on the survey form display area 740.

Two kinds of marks are attached to items by the logic check at the "PATIENT-BACKGROUND" page of the survey form display area 740. Δ marks 744 through 746 show the error item detected by the predetermined logic check.

The pharmaceutical manufacturer person in charge can confirm the contents of the error by the logic check by clicking the Δ marks. For example, the pharmaceutical manufacturer person in charge clicks the ▲ mark 745, and then, the confirmation contents screen 750 as shown in FIG. 21A is displayed.

Referring to FIG. 21A, the confirmation contents screen 750 includes a current logic check result 758 that displays information concerning a current logic check error, and a previous logic check result 759 that displays information concerning a previous logic check error. When the current logic check error is detected at the first time, the logic check result 759 is not displayed. When the current logic check error is detected for more than three times, each logic check result is displayed for each time.

The current logic check result 758 includes subject items 751 that are subject to the logic check error, error information 752 showing contents of the current logic check error, an input area 753 for inputting request contents from a verifier to the medical doctor in charge with respect to the current logic check error, a save button 754 for saving error contents that are inputted, and a close button 755 for closing a screen without saving.

The error information 752 includes items of "CONFIRMATION" check box, "ERROR CODE" specifying an error, "ERROR MESSAGE" showing the error contents, "DATA" showing data being inputted, and a like. When the error message is informed to the medical doctor in charge, a check mark is applied to the "CONFIRMATION" check box.

The previous logic check result 759 includes error information 757 that shows contents of the logic check error, and a display area 757 that displays previous request contents.

The pharmaceutical manufacturer person in charge confirms the contents of the logic check error on the confirmation contents screen 750, inputs request contents, which prompts the medical doctor in charge to modify, into the input area 753, and clicks the save button 754 after applying the check mark to the "CONFIRMATION" check box of the error information 752. The storing process confirmation screen 760 as shown in FIG. 21B is displayed when the save button 754 is clicked.

Referring to FIG. 21B, the storing process confirmation screen 760 includes a display area 761 that shows the contents of the logic check, a display area 762 that displays the request contents inputted by the pharmaceutical manufacturer person in charge, and a close button 763 for closing the screen.

The pharmaceutical manufacturer person in charge confirms contents saved by the storing process confirmation screen 760, that is, the contents that are attached with the survey form at the re-survey request and informed to the medical doctor in charge. Then, the pharmaceutical manufacturer person clicks the close button 763. The pharmaceutical manufacturer person in charge conducts the same process for Δ marks 743 and 746 displayed on the survey form display area 740 of the survey form information screen 730 of FIG. 20, based on the confirmation contents screen 750 and the storing process confirmation screen 760.

Moreover, in the survey-form display area 740, items attached with "!" marks 747 and 748 are not items that are not detected by the logic checking part 404 of the pharmaceutical manufacturer side processing part 400 of FIG. 5 but are formed so as to enable the pharmaceutical manufacturer person in charge to input supplemental contents.

By clicking these "!" marks 747 and 748, the pharmaceutical manufacturer person in charge can input request matters with respect to the medical doctor in charge, corresponding to the items. For example, when the pharmaceutical manufacturer person in charge clicks the "!" mark 747, a confirmation contents screen 765 as shown in FIG. 22 is displayed.

Referring to FIG. 22, the confirmation contents screen 765 includes a target subject item 766, an input area 768 for inputting the supplemental contents from the pharmaceutical manufacturer person in charge to the medical doctor in charge, a save button 769 for saving the supplemental contents being inputted, and a close button 770 for closing the screen without saving.

The pharmaceutical manufacturer person in charge inputs the supplemental contents into the input area 768, and clicks the save button 769. Then, the supplemental contents are attached with the survey form at the re-survey request.

In the following, in the operating procedure 28 of FIG. 2, a modifying process conducted by the medical doctor in charge of the survey form for which the pharmaceutical manufacturer person in charge requested the re-survey will be described.

Screens for the re-survey provided to the medical doctor terminal will be described with reference to FIG. 23A through FIG. 23C.

In FIG. 23A, a protocol list table 772 showing another example of the protocol list surveyed by the medical doctor in charge is shown in the protocol selection screen 600 including the same display configuration as that of FIG. 11.

When the medical doctor in charge clicks the "NEW ARRIVAL" item (value 2) corresponding to the protocol name "MEDICINE ABC", the patient selection screen 650 shown in FIG. 23B having a display configuration equivalent to that of FIG. 17A is displayed.

In FIG. 23B, for example, the medical doctor in charge clicks the status 776 (NEW ARRIVAL) corresponding to a patient name "FUJI, TARO" from a case list 775 that includes an item configuration equivalent to that of FIG. 17A. The medical doctor in charge clicks status 776 and then, the survey form selection screen 655 shown in FIG. 23C showing a display configuration equivalent to that of FIG. 17B is displayed. In this case, in an operation item 777 including an item configuration equivalent to that of FIG. 17B, a send item value and a delete item value are "NOT AVAILABLE". That is, when a send status value is the "NEW ARRIVAL", the medical doctor in charge cannot send and delete this survey form.

Therefore, it is possible to prevent incorrectly deleting (losing) the survey form.

Figure 24:
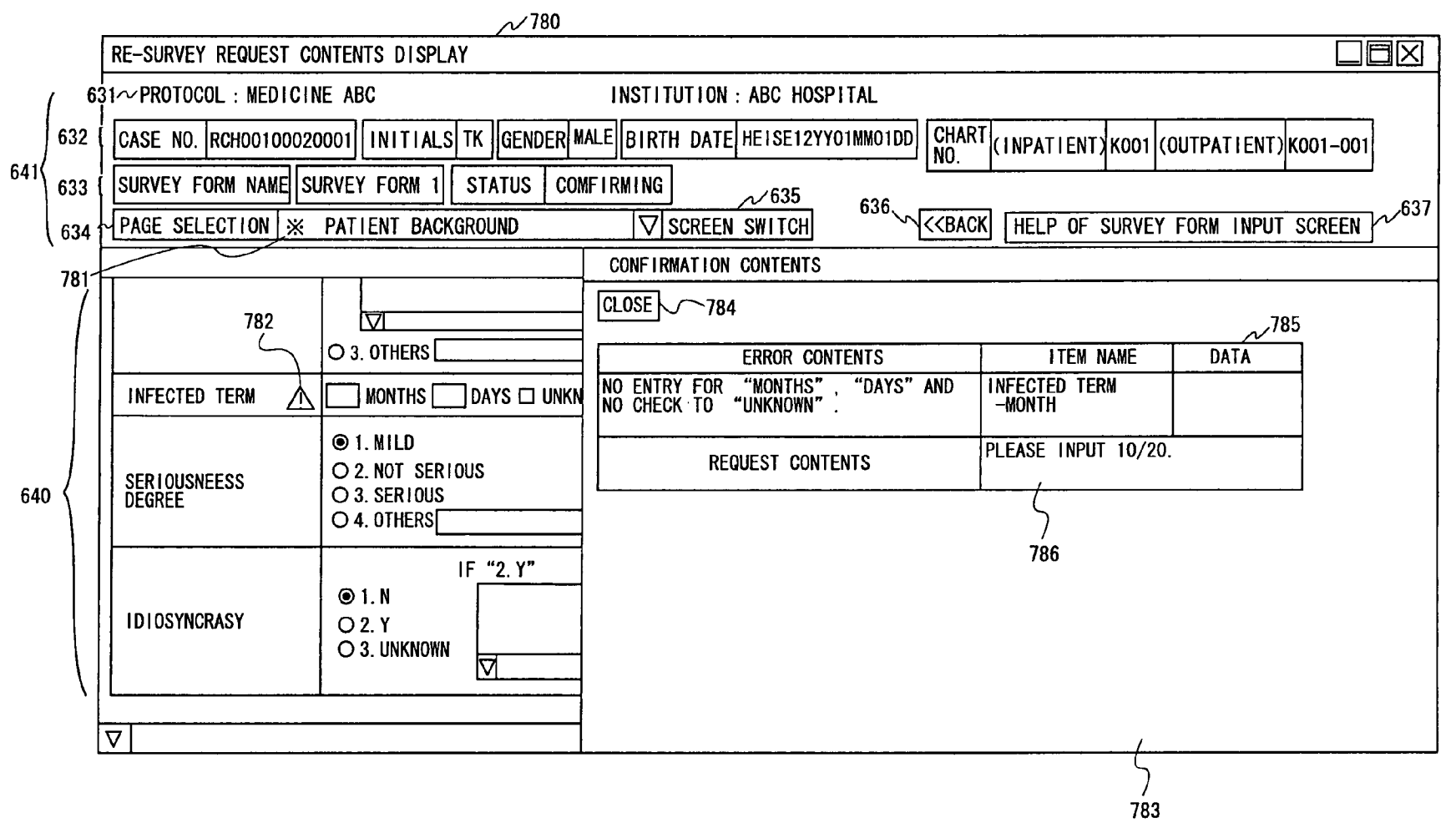

In FIG. 23C, for example, when the medical doctor in charge clicks the status item value 778 (NEW ARRIVAL) from the operation item 777 including an item configuration equivalent to that of FIG. 17B, a re-survey request contents display screen as shown in FIG. 24 is displayed.

FIG. 24 is a diagram showing an example of the re-survey request contents display screen.

In FIG. 24, the re-survey request contents display screen 780 shows a display configuration equivalent to that of the survey form information input 630 as the first example of FIG. 13. However, in the page selected at the page selection 634, a page name attaching with a "⋅✗⋅" may be displayed. The page name attaching with the "⋅✗⋅" shows that there is an item where the request contents or supplemental contents are attached by the pharmaceutical manufacturer person in charge.

Therefore, it is possible for the medical doctor in charge to recognize that there is a page to modify by the page selection 634.

The medical doctor in charge displays a "⋅✗⋅ PATIENT BACKGROUND" page on the survey form input area 640 by clicking the screen switch button 635, and confirms the items attached with the "!" marks in the "⋅✗⋅ PATIENT BACKGROUND" page displayed in the survey form input area 640.

When the medical doctor clicks the "!" mark, a confirmation contents screen 783 is displayed.

The confirmation contents screen 783 includes a close button 784 for closing the screen, and a display area 785 that shows the request contents.

The display area 785 includes items of "ERROR CONTENTS" showing error contents, "ITEM NAME" where an error is detected, "DATA" inputted by the medical doctor, "REQUEST COMMENTS" that is inputted by the pharmaceutical manufacturer person in charge for the medical doctor, and a like. In this case, it is understood that there is no entry in the infected term and the "UNKNOWN" is not checked, and that the pharmaceutical manufacturer person requests to input "10/20".

After confirming the request contents, the medical doctor in charge clicks the close button 784, and inputs "10/20" into the items, with which the "!" marks are attached, in the "PATIENT BACKGROUND" page displayed in the survey form input area 640 of the re-survey request contents display screen 780, based on the request contents. When the medical doctor completes inputting all items with the "!" marks, the medical doctor clicks a save button (not shown) and ends modifying the "PATIENT BACKGROUND" page.

When the medical doctor in charge clicks the save button, the survey form information correcting part 308 of the medical doctor side processing part 300 shown in FIG. 5 is activated. The medical doctor in charge stores item data modified based on the request contents in the survey form information table 133.

The medical doctor in charge sends this survey form to the pharmaceutical manufacturer person in charge after modifying the survey form (the operating procedure 29 in FIG. 2).

The medical doctor in charge clicks an item value, which is not sent but should be sent, corresponding to the protocol from the protocol list table 772 of the protocol selection screen 600 by the same operation as the operating procedure 26. In the case list 775 of the patient selection screen 650, the medical doctor in charge selects a patient. In this case, the re-survey selection screen 655 as shown in FIG. 25 is displayed.

In the re-survey selection screen 655 of FIG. 25A, the operation item 788 including the item configuration equivalent to that of FIG. 17B can be sent but not deleted with respect to the survey form name "SURVEY FORM NAME 1".

The medical doctor in charge clicks a send item value 789 of the operation item 778. In the confirmation screen 661 displayed by this click, the medical doctor clicks the OK button 662. Then, the selected survey form is sent (the operating procedure 29 in FIG. 2).

When the survey form is sent, as shown in FIG. 25B, the status item value of the operation item 788 of the survey form selection screen 655 is set as the "SENT", and the send item value is set as the "NOT AVAILABLE". Furthermore, a message 790 showing that it completed sending the survey form is displayed.

When the pharmaceutical manufacturer person in charge selects a plurality of the survey forms and conducts the re-survey requests to the medical doctors in charge as mentioned above, one e-mail grouping the re-survey requests by the medical doctors is sent.

As described above, the survey form is repeatedly modified until it is completed to input into the survey form between the pharmaceutical manufacturer person in charge and the medical doctor in charge.

As described above, all modification of the survey form that is repeated can be conducted by using screens provided by the survey form managing system. Therefore, the pharmaceutical manufacturer person in charge is not required to visit the medical doctor in charge for each re-survey request repeatedly.

Moreover, the request contents or the supplemental contents can be attached for each item to be modified by the medical doctor in charge. Furthermore, the medical doctor in charge can refer to the request contents or the supplemental contents at the display position of the item only by clicking the mark attached with the item.

Next, the survey form managing system additionally providing a function for improving confidentiality of the survey form to be edited and a function for analyzing and summarizing based on data of the survey form provided by the medical doctor in charge will be described.

Figure 26:
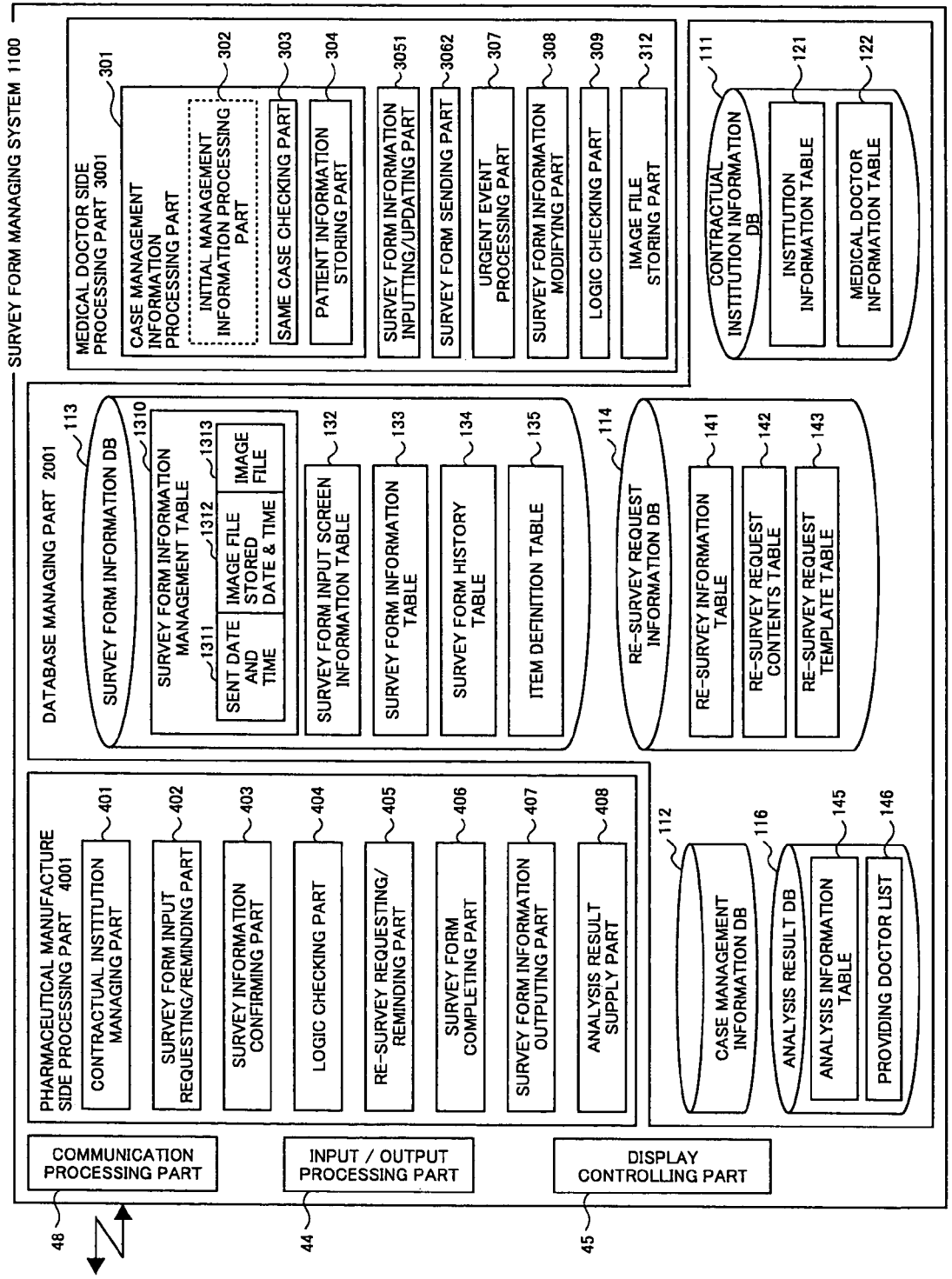
FIG. 26 is a diagram showing another example of a functional configuration of a survey form managing system.

FIG. 26 is a diagram showing another example of the functional configuration of the survey form managing system. In FIG. 26, parts that are the same as the ones in FIG. 5 are indicated by the same reference numerals and the explanation thereof will be omitted.

Referring to FIG. 26, in differences from the medical doctor side processing part 300 of the survey form managing system 100 shown in FIG. 5, a medical doctor side processing part 3001 of a survey form managing system 1100 includes a survey form information inputting/updating part 3051 that prevents the falsification of the survey form based on signature information of the medical doctor, a survey form sending part 3062 that manages sent date and time of the survey form, and an image file storing part 312 that manages an image file of a completed survey form. Moreover, in differences from the pharmaceutical manufacturer side processing part 400 of the survey form managing system 100 shown in FIG. 5, the pharmaceutical manufacturer side processing part 4001 of the survey form managing system 1100 further includes an analysis result supply part 408 that provides analysis result analyzed based on the survey form in the pharmaceutical manufacturer to the medical doctor.

Moreover, in difference from the database managing part 200 of the survey-form managing system 100 shown in FIG. 5, the database managing part 2001 of the survey form managing system 1100 includes a survey form management information table 1310 of the survey form information DB 113 that manages an image file for each survey form, and an analysis result DB 116 that manages to provide the analysis result of the survey form by the pharmaceutical manufacturer to the medical doctor.

Processes in the survey form sending part 3062 and the image file storing part 312 will be described.

Figure 27A:
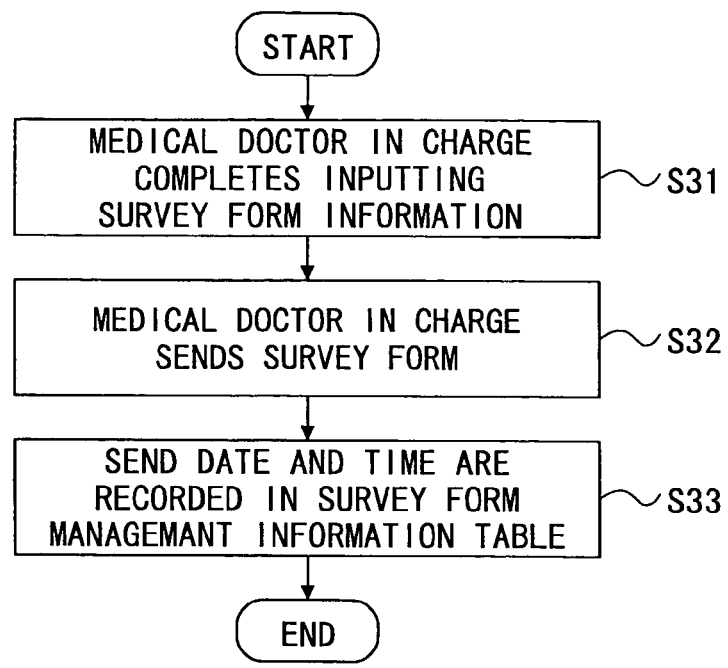
FIG. 27A is a flowchart diagram explaining a process in a survey form transmitting part.
Figure 27B:
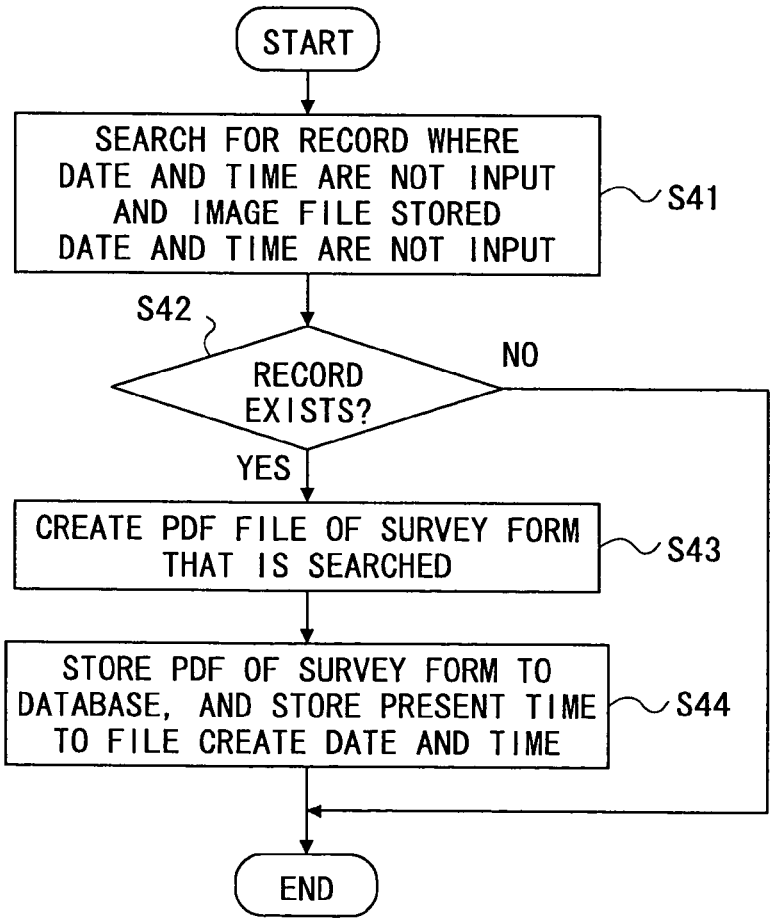
FIG. 27B is a flowchart diagram explaining a process in an image file storing part.

In FIG. 27A and FIG. 27B, flowcharts for explaining examples of a process for creating the image file of the survey form are shown.

FIG. 27A is a flowchart diagram for explaining the process by the survey form sending part.

Referring FIG. 27A, the medical doctor in charge completes inputting the survey form information (step S31) and sends the survey form (step S32). The survey form sending part 2062 stores a current time in the sent date and time of the survey form managed in the survey form management information table 1310.

Furthermore, the image file storing part 312 is executed for example, for each 15 second and conducts in accordance with a flowchart shown in FIG. 27B, in order to create the image file of the survey form that has already sent.

FIG. 27B is a flowchart diagram for explaining a process by the image file storing part.

Referring to FIG. 27B, the image file storing part 312 searches for a record, in which the sent date and time are not inputted and the image file stored date and time are not inputted, from the survey form management information table 1310 (step S41).

By the step S41, it is checked whether or not the records are found (step S42). The process is terminated when no record is found. On the other hand, when the records are found, the survey form information is obtained from the survey form information table 133 based on the protocol ID identifying the protocol and the survey form ID identifying the survey form from the found records and a PDF file is created based on the survey form information (step S43).

The PDF file of the survey form created at the step S43 is stored in the survey form management information table 1310 as an image file of the survey form, and the present time is stored in image file creation time (step S44).

Next, a process of the survey form information inputting/updating part 3051 will be described with reference to FIG. 28.

Figure 28:
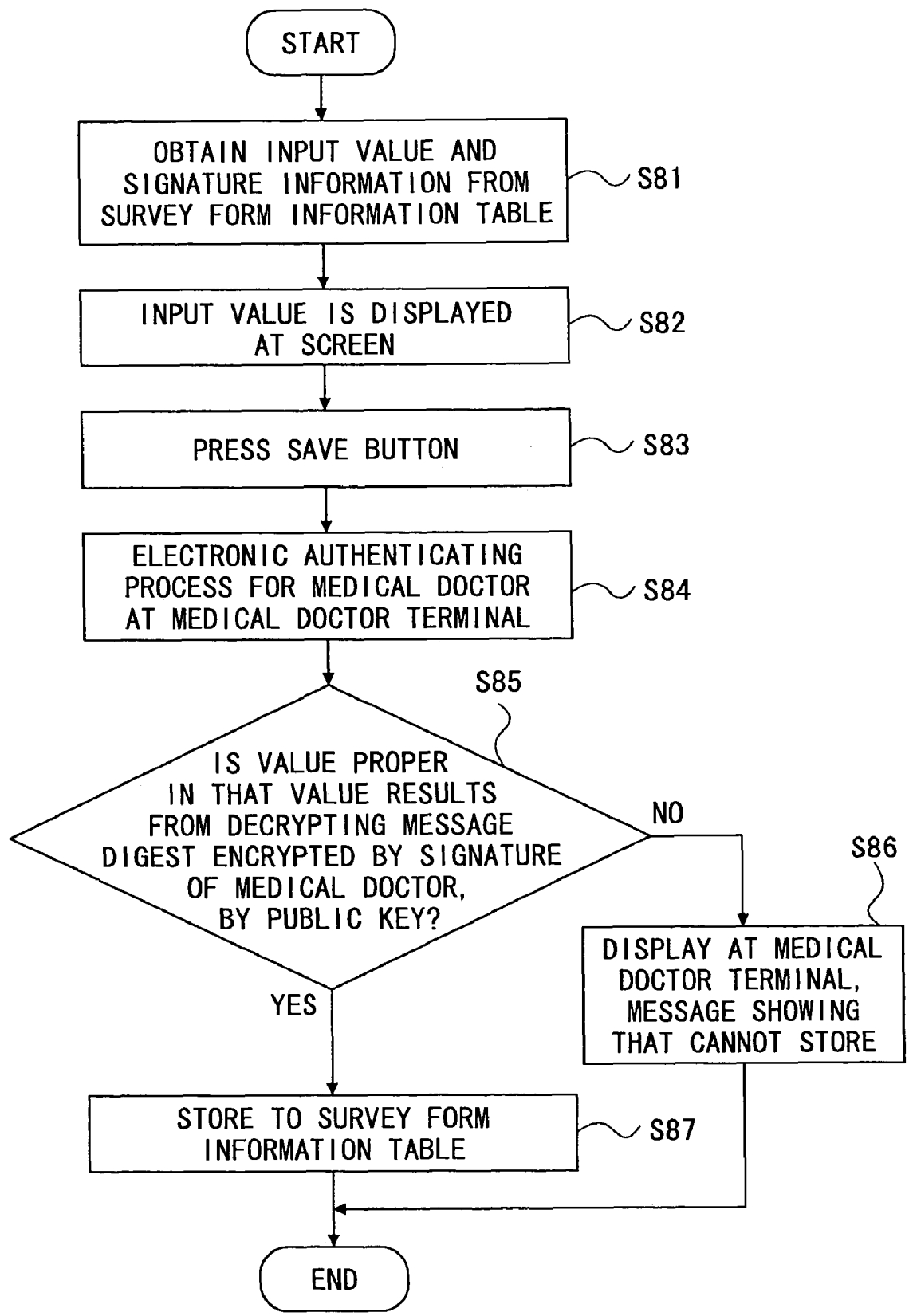
FIG. 28 is a flowchart diagram showing an example of a survey form managing process.

FIG. 28 is a flowchart diagram showing an example of the survey form managing process.

Referring to FIG. 28, the survey form information inputting/updating part 3051 obtains an input value and signature information from the signature information DB 115 (step S81). In a case of inputting a new survey form, the input value and the signature information are blank.

The obtained input value is displayed at the medical doctor terminal 30 (step S82).

When the medical doctor in charge presses a save button after inputting the survey form information (step S83), an electronic authentication process is executed at the medical doctor terminal 30, a message digest encrypted with a private key of the medical doctor is attached to the survey form information, and the survey form is sent to the survey form managing system 100 (step S84). The survey form information inputting/updating part 3051 determines whether or not a value is proper in that the value results from decrypting the message digest encrypted with the private key of the medical doctor, by a public key of the signature information of the medical doctor (step S85). When the value is not proper, a message showing that the survey form information cannot be stored is displayed at the medical doctor terminal 30 (step S86) and the process is terminated. On the other hand, when the value is identical, the input value and the signature information are stored in the signature information DB 115 (step S87), and the process is terminated.

By the above-mentioned survey form managing process, it can prevent that the survey form sent by the medical doctor in charge is falsified and also, it can authenticate whether it is the survey-form information inputted by the medical doctor in charge. Only in a case in which the survey form is not falsified and the medical doctor in charge is authenticated, the survey form information is updated.

FIG. 29 is a diagram showing an example of a data structure of the survey form-information record.

Referring to FIG. 29, the survey form information record managed on the survey form information table 113 includes an item 61 that shows data No. as a sequence number of item data, an item 62 that shows the input value that is inputted by the medical doctor in charge when the survey form is sent, an item 63 that shows a version no. of the survey form, an item 64 with the message digest (MD) that shows code information, and an item 65 that shows the signature of the medical doctor.

The item 64 shows the MD information encrypted with the private key of the medical doctor.

The item 65 is information for authenticating the medical doctor with the public key of the medical doctor published by the certificate authority.

In the steps S83 and S84 of FIG. 28, the information to items 61 through 65 are sent to the survey form managing system 1100, when the medical doctor clicks the save button. In the step S85 of FIG. 28, when the input value and the signature information that is inputted by the medical doctor are identical, the items 61 through 65 are stored in the survey form information table 133 as one record.

Next, a method for providing the analysis result of the survey form by the pharmaceutical manufacturer will be described with reference to FIG. 30A and FIG. 30B.

Figure 30A:
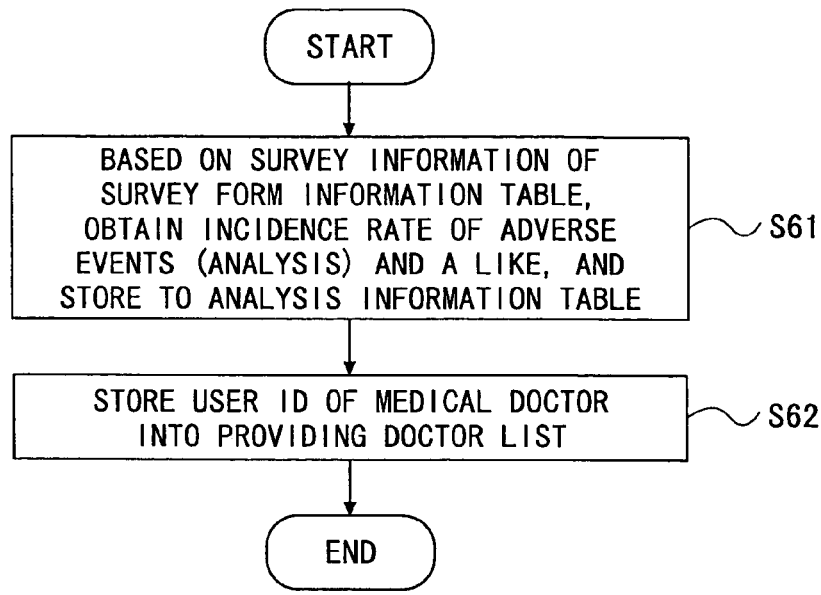
FIG. 30A is a flowchart diagram explaining registration of an analysis result by the pharmaceutical manufacturer.

FIG. 30A is a flowchart diagram for explaining a registration of the analysis result by the pharmaceutical manufacturer.

Referring to FIG. 30A, the pharmaceutical manufacturer analyzes an incidence rate and a like based on the survey form information stored in the survey form information table 133, stores the analysis result in the analysis information table 145 of the analysis result DB 116 (step S61), and registers the user ID of the medical doctor in charge, who is allowed to refer to this analysis result, into a providing medical doctor list 146 (step S62).

Figure 30B:
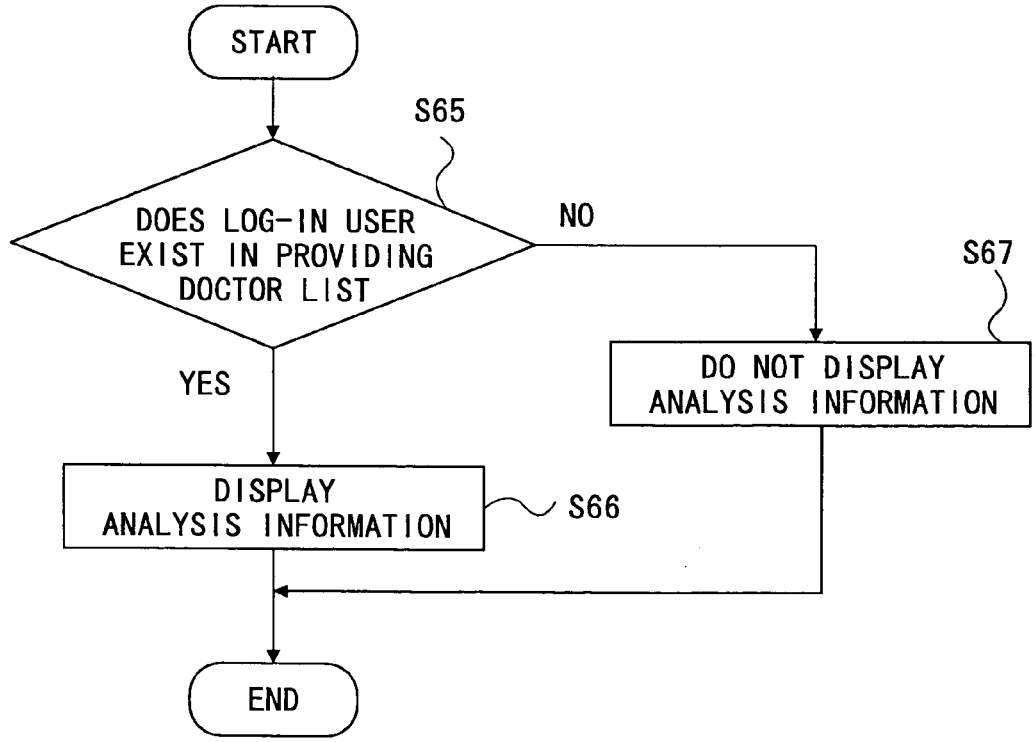
FIG. 30B is a flowchart diagram explaining a process by an analysis information providing part.

FIG. 30B is a flowchart diagram for explaining a process by the analysis information providing part.

Referring to FIG. 30B, the analysis result supply part 408 determines whether or not the user ID of the medical doctor in charge who logs in is registered (step S65). When the user ID is registered, the analysis information is displayed at the medical doctor terminal 30, and then, the medical doctor can download the analysis information (step S66). On the other hand, when the user ID is not registered, the analysis information is not displayed, and a message showing that the analysis information is not displayed is displayed at the medical doctor terminal 30 (step S67).

Therefore, for example, the pharmaceutical manufacturer can limit to the medical doctors in charge to whom the survey form is requested, to provide the analysis result of the survey form.

In the above-mentioned embodiment, since information inputted into items of the survey form by the medical doctor in charge can be directly managed, the pharmaceutical manufacturer person in charge is not required to visit the medical doctor and it is not required for a plurality of pharmaceutical manufacturer persons to input data of the survey form. Moreover, input errors by the pharmaceutical manufacturer person in charge cannot occur. Therefore, it is possible to reduce a large amount of workload and it is possible to obtain real data inputted by the medical doctor in charge.

Since the patient name inputted by the medical doctor in charge is automatically converted into the initials, the medical doctor in charge can input a full name of the patient into the survey form. In addition, when the case is registered to the survey form managing system, an encrypted full name and the converted initials of the patient are stored. Therefore, it is possible to protect secrecy of private information.

Moreover, since the medical doctor in charge can manage, by the unified survey form status, the survey forms requested from a plurality of pharmaceutical manufacturer persons in charge, the survey forms can be easily managed. Similarly, since the pharmaceutical manufacturer person in charge can manage as the survey form status that unifies the requests to a plurality of medical doctors in charge, the survey forms can be easily managed.

In the above-mentioned embodiment, the present invention is applied to the post-marketing surveillance for collecting information including the adverse drug reactions in practical use in a certain adaptation after the adaptation is certified and marketed. However, it is not limited to this post-marketing surveillance. For example, in the future, the present invention can be applied to a clinical test by which it reasons how to treat the patients, with respect to general patients who are needed to be treated as a population based on samples of limited patients.

As described above, according to the present invention, it is possible to request the re-survey to an implementer while the re-survey is required with respect to the survey form sent by the implementer, and the completed survey form is maintained with the version number. Therefore, a verifier is not required to visit the implementer for many times to obtain the survey form until the survey form is completed, and it is not required to input data of the survey form by a plurality of the verifiers. Moreover, since the completed survey form is stored with the version number, a version management can be automatically conducted. Furthermore, since a manager of the data verification supporting server can be separated from the implementer and the verifier, it is possible to guarantee reliability of information of the survey form. Moreover, since the data verification supporting server can be arranged so as to conduct an authentication based on authentication information of the implementer attached to the survey form, it is possible to guarantee the reliability of the information of the survey form even if the data verification supporting server is arranged at a verifier side.

Moreover, according to the present invention, when a person name is inputted at a terminal side where the private information is inputted, the person name is converted into the initials. Also, in a case in which the private information is managed, the private information is managed by the encrypted person name and the converted person name. Furthermore, the information managing server can be controlled so that the private information is provided with the private name to a first user who inputted the private information while the private information is provided with the initials to a second user who receives the private information.

The invention claimed is:

1. A data verification progress managing and supporting server, which is an Application Service Provider (ASP) server for managing a data verification progress and supporting a plurality of implementers and a plurality of verifiers to verify data which is inputted to each item of a survey form for surveying an effect of implementing a product, said data verification progress managing and supporting server comprising:
    a survey form managing part managing the survey form which is inputted by an implementer and sent from an implementer terminal of the implementer through the Internet, based on a protocol by a survey form information database which manages the survey form based on the protocol;
    a re-survey information managing part informing through the Internet the implementer of a re-survey inquiry based on a re-survey inquiry request for requesting a re-survey, which is received from a verifier terminal of a verifier verifying the survey form, said re-survey inquiry request indicating the implementer who sent the survey form, and storing a request count as the version information by corresponding to the survey form;
    a contractual institution information managing part managing information for each institution and each implementer based on the protocol by a contractual institution information database;
    a survey management screen displaying part displaying a survey management screen showing a first status list of the survey forms for each institution based on the protocol at the implementer terminal and a second status list of the survey forms for each implementer and each institution at the verifier terminal by using the survey form information database and the contractual institution information database;
    and a survey form maintaining part maintaining the survey form and said version information managed by said re-survey form managing part when notification of a verification completion of the survey form is received from the verifier terminal,
    wherein said survey form managing part changes an implementer status to indicate in the first status list and a verifier status to indicate in the second status list by associating with operating procedures performed by the implementer and the verifier until the verification completion for each survey form, and restrains the implementer and the verifier from inputting, saving or referring to information of the survey form according to the implementer status and the verifier status respectively, in a unified survey form status, and
    wherein when the verifier inputs a survey form collection not-available day and a collection not-available reason in case in that the implementer cannot proceed the surveying an effect of implementing the product, said survey form managing part changes the implementer status to indicate that the verifier has received the survey form and the verifier status to indicate that the survey form is not available, and allows the implementer and the verifier to only refer to the survey form.

2. The data verification supporting server as claimed in claim 1, wherein said survey management screen shows a number of the survey forms corresponding to each status item of the verifier status in the status list.

3. The data verification supporting server as claimed in claim 1, further comprising a protocol selection screen displaying part displaying a protocol selection screen showing a number of the survey forms corresponding to each status item of the implementer status at the implementer terminal.

* * * * *